US012693436B2

(12) United States Patent
Han et al.

(10) Patent No.: US 12,693,436 B2
(45) Date of Patent: Jul. 28, 2026

(54) SCINTILLATION CRYSTAL ARRAY, DETECTOR, MEDICAL IMAGING DEVICE, AND MANUFACTURING METHOD

(71) Applicant: Beijing Hamamatsu Photon Techniques INC., Beijing (CN)

(72) Inventors: Yongfei Han, Beijing (CN); Suilao Yao, Beijing (CN); Deyu Cao, Beijing (CN); Ruipeng Zhu, Beijing (CN)

(73) Assignee: Beijing Hamamatsu Photon Techniques INC., Beijing (CN)

( * ) Notice: Subject to any disclaimer, the term of this patent is extended or adjusted under 35 U.S.C. 154(b) by 143 days.

(21) Appl. No.: 18/729,165

(22) PCT Filed: Mar. 24, 2023

(86) PCT No.: PCT/CN2023/083647
§ 371 (c)(1),
(2) Date: Jul. 15, 2024

(87) PCT Pub. No.: WO2023/179761
PCT Pub. Date: Sep. 28, 2023

(65) Prior Publication Data
US 2025/0180761 A1     Jun. 5, 2025

(30) Foreign Application Priority Data

Mar. 25, 2022   (CN) ........................ 202220678767.X
Jun. 16, 2022   (CN) ........................ 202210683091.8

(51) Int. Cl.
| | |
|---|---|
| *G01T 1/202* | (2006.01) |
| *G01T 1/20* | (2006.01) |
| *A61B 6/03* | (2006.01) |

(52) U.S. Cl.
CPC ............ *G01T 1/202* (2013.01); *G01T 1/2018* (2013.01); *A61B 6/037* (2013.01)

(58) Field of Classification Search
CPC ..... G01T 1/202; G01T 1/2018; G01T 1/2002; G01T 1/2985; G01T 1/2921; A61B 6/037
See application file for complete search history.

(56) References Cited

U.S. PATENT DOCUMENTS

2009/0236534 A1   9/2009   Selfe et al.
2009/0294683 A1   12/2009   Perna
(Continued)

FOREIGN PATENT DOCUMENTS

CN    101779145 A    7/2010
CN    103954989 A    7/2014
(Continued)

OTHER PUBLICATIONS

International Search Report on Patentability issued on Jul. 4, 2023, in corresponding International Application No. PCT/CN2023/083647, 8 pages.
(Continued)

*Primary Examiner* — Kiho Kim
(74) *Attorney, Agent, or Firm* — Maier & Maier, PLLC

(57) ABSTRACT

A scintillation crystal array, a detector, and a manufacturing method solve the image distortion problem in PET caused by ESR layers. The scintillation crystal array includes a plurality of scintillation crystal units, a gap is provided between each two adjacent scintillation crystal units, first reflecting layers are arranged in a part of the gaps of the scintillation crystal array, and second reflecting layers are arranged in a part of the gaps. The first reflecting layers are made of a thin film-like material, and the second reflecting layers are made of an amorphous material. By filling the gaps between the scintillation crystal units with the two types of reflecting layers, it becomes possible to leverage the high reflectivity of the thin film-like material while preventing issues in the scintillation crystal array.

13 Claims, 16 Drawing Sheets

(56)　　　　References Cited

U.S. PATENT DOCUMENTS

| | | | |
|---|---|---|---|
| 2010/0148074 A1 | 6/2010 | Menge et al. | |
| 2010/0217112 A1 | 8/2010 | Choi et al. | |
| 2011/0017916 A1 | 1/2011 | Schulz et al. | |
| 2012/0001078 A1* | 1/2012 | McEvoy | G01T 1/2002 |
| | | | 250/366 |
| 2013/0193331 A1* | 8/2013 | Perna | G01T 1/2002 |
| | | | 250/366 |
| 2016/0170041 A1 | 6/2016 | Lee | |
| 2021/0015436 A1 | 1/2021 | Wang et al. | |

FOREIGN PATENT DOCUMENTS

| | | |
|---|---|---|
| CN | 106842384 A | 6/2017 |
| CN | 107167832 A | 9/2017 |
| CN | 107290771 A | 10/2017 |
| CN | 107688193 A | 2/2018 |
| CN | 109856665 A | 6/2019 |
| CN | 109991648 A | 7/2019 |
| CN | 110376633 A | 10/2019 |
| CN | 210626673 U | 5/2020 |
| CN | 113176604 A | 7/2021 |
| CN | 115220084 A | 10/2022 |
| CN | 218037369 U | 12/2022 |
| WO | 2013054300 A2 | 4/2013 |

OTHER PUBLICATIONS

Office Action issued on Oct. 26, 2024, in corresponding Chinese Application No. 202210683091.8, 9 pages.
Search Report issued on Oct. 26, 2024, in corresponding Chinese Application No. 202210683091.8, with partial English translation, 2 pages.
Supplementary Search Report issued on Nov. 26, 2024, in corresponding Chinese Application No. 2022106830918, 6 pages.
Feng et al., "Effect of Crystal Surface Characteristics on the Performance of PET Detectors", Nuclear Techniques, China Academic Journal Electronic Publishing House, Jun. 2017, vol. 40, No. 6, 7 pages, with partial English translation.
Wei et al., "Performance Evaluation of a PET Detector with a Sparse Si PM Array and Gap Reflectors", J. Tsinghua Univ (Sci & Technol), China Academic Journal Electronic Publishing House, ISSN: 1000-0054, Sep. 4, 2018, vol. 58, No. 10, pp. 929-933, with partial English translation.
Chen et al., "Comparative Study of NaI, BGO, LSO, GSO and YSO Scintillators Using Monte Carlo Simulations", Optical Instruments, ISSN: 1005-5630, Aug. 2005, vol. 27, No. 4, 4 pages, with partial English translation.
Li et al., "Study on LSO Crystal and Its Array Finishing Technology", Piezoelectrics & Acoustooptics, China Academic Journal Electronic Publishing House, ISSN: 1004-2474, Jun. 2013, vol. 35, No. 3, 4 pages, with partial English translation.

* cited by examiner

50

F

52

51

SCINTILLATION CRYSTAL ARRAY, DETECTOR, MEDICAL IMAGING DEVICE, AND MANUFACTURING METHOD

This application claims the priority of China Patent Application No. 202220678767.X, entitled "SCINTILLATION CRYSTAL ARRAY, DETECTOR, AND MEDICAL IMAGING DEVICE", filed on Mar. 25, 2022, and China Patent Application No. 202210683091.8, entitled "SCINTILLATION CRYSTAL ARRAY, DETECTOR, MEDICAL IMAGING DEVICE, AND MANUFACTURING METHOD", filed on Jun. 16, 2022, the entire contents of which are incorporated herein by reference.

TECHNICAL FIELD

The application relates to the technical field of radiation detection, in particular to a scintillation crystal array, a detector, a medical imaging device, and a manufacturing method.

BACKGROUND

Positron emission computed tomography (PET) is a new imaging technology that allows for the visualization of metabolism of biomolecules, receptors, and neurotransmitter activity in living organisms. It is widely used in the diagnosis and differential diagnosis of various diseases, assessment of disease status, evaluation of treatment efficacy, organ function studies, and new drug development.

During PET imaging, a radioactive drug labeled with a nuclide is injected into the organism, and this radioactive drug accumulates in the diseased tissue or organ. The radioactive nuclide carried by the drug undergoes decay and emits positrons, which then annihilate with negatrons in the body, releasing a pair of $\gamma$ photons with almost opposite directions. After being emitted from the subject's body, the two $\gamma$ photons are captured by scintillation crystals of a ring-shaped detector, emitting scintillation light. A photoelectric sensor collects the scintillation light and converts it into readable electrical signals. The position and energy information of the 7 photons can be obtained through the electrical signals, thereby obtaining a tomographic distribution map of the positron nuclide within the organism.

The scintillation crystal refers to a crystal that can transform the kinetic energy of high-energy particles into light energy and emit a flash under the impact of high-energy particles. The scintillation crystal can be used to detect X-rays, $\gamma$-rays, neutrons and other high-energy particles. Detection and imaging technologies based on scintillation crystals has been widely used in nuclear medicine, high-energy physics, safety inspection, industrial nondestructive testing, space physics and nuclear prospecting.

In PET, scintillation crystals are typically stacked as an array to capture positional information. A scintillation crystal array is a multi-unit structure including multiple scintillation crystal units arranged in a linear or planar array format. When arranged in a linear fashion, it is referred to as a one-dimensional array scintillator, and when arranged in a planar array, it is known as a two-dimensional scintillation crystal array. These array blocks are installed in PET scanners, forming detector rings of different sizes, and serve as the essential component for radiography detection.

In PET, it is crucial for the scintillation crystal array to possess an ultra-precise light collection efficiency in order to support ultra-precise PET imaging, such as ultra-precise small animal PET imaging. A reflecting layer in the scintillation crystal array plays a critical role in enhancing the light collection efficiency. Therefore, careful selection of the optimal reflecting layer is necessary to ensure that the scintillation crystal array meets the requirements, such as an ultra-small 16*16 channel scintillation crystal array with individual pixel size measuring only 0.25*0.25 mm.

FIGS. 12 and 13 depict typical scintillation crystal array products in this technical field. In FIG. 12, gaps between the scintillation crystal units 40 in the scintillation crystal array 400 are filled with barium sulfate reflecting layers 41, such as the scintillation crystal array disclosed in CN107003218A. However, the reflectivity of the barium sulfate reflecting layer 41 is approximately 93%, which is lower than that of an enhanced specular reflector (ESR). Moreover, the barium sulfate reflecting layer 41 is difficult to process and can hardly achieve a uniform thickness due to its fluidity or plasticity.

In FIG. 13, gaps between the scintillation crystal units 50 in the scintillation crystal array 500 are filled with ESR reflecting layers 51, such as the scintillation crystal array disclosed in CN106646581B. The advantage of this approach is that the ESR reflecting layer 51 does not have fluidity or plasticity, making it easier to process and ensuring a uniform thickness. Additionally, the reflectivity of ESR can reach up to 98%. When applied in regular scintillation crystal arrays, it enables more scintillation light to be reflected and collected by optical detectors, thereby improving the signal-to-noise ratio and detector efficiency. However, the inventors have discovered that when the ESR reflecting layer 51 is applied to ultra-small scintillation crystal arrays ($\leq 0.5$ mm), it not only fails to exhibit the advantage of high reflectivity but also results in significant distortion in PET images. This problem needs to be urgently resolved.

SUMMARY

Embodiments of the application provide a scintillation crystal array, a detector, a medical imaging device, and a manufacturing method that can solve the problem of image distortion in PET caused by the use of an ESR reflecting layer in a scintillation crystal array in the prior art.

In a first aspect, a scintillation crystal array is provided, which comprises a plurality of scintillation crystal units, a gap is provided between each two adjacent scintillation crystal units, first reflecting layers are arranged in a part of the gaps of the scintillation crystal array, and second reflecting layers are arranged in a part of the gaps. The first reflecting layers are made of a thin film-like material, and the second reflecting layer are made of an amorphous material.

Alternatively, the scintillation crystal array comprises first gaps arranged in a first direction and second gaps arranged in a second direction; and a part of intersecting first gaps and second gaps in the scintillation crystal array are respectively provided with the first reflecting layers and the second reflecting layers; or all intersecting first gaps and second gaps in the scintillation crystal array are respectively provided with the first reflecting layers and the second reflecting layers.

Alternatively, in a case where a part of intersecting first gaps and second gaps in the scintillation crystal array are respectively provided with the first reflecting layers and the second reflecting layers, the second reflecting layers are arranged in gaps in the scintillation crystal array except the said part of intersecting first gaps and second gaps.

Alternatively, in the first gaps and the second gaps respectively provided with the first reflecting layers and the second reflecting layers, all the first gaps are provided with the first reflecting layers and all the second gaps are provided with the second reflecting layers, or all the first gaps are provided with the second reflecting layers and all the second gaps are provided with the first reflecting layers.

Alternatively, the first reflecting layers comprise one or more of: ESR reflecting layers, polyethylene terephthalate reflecting layers, polytetrafluoroethylene film reflecting layers, aluminum foil reflecting layers and aluminum-plated plastic reflecting layers.

Alternatively, the second reflecting layers comprise one or more of: reflecting layers made of powder materials, reflecting layers made of liquid materials, reflecting layers made of a mixture of powder materials and liquid materials, and reflecting layers made of paste materials.

Alternatively, the second reflecting layers comprise one or more of: barium sulfate reflecting layers, titanium dioxide reflecting layers, magnesium oxide reflecting layers and polytetrafluoroethylene powder reflecting layers.

Alternatively, a thickness of the gap is greater than or equal to 0.01 mm and less than or equal to 0.5 mm.

In a second aspect, a detector is provided, comprising the scintillation crystal array as described above.

In a third aspect, a medical imaging device is provided, comprising the detector as described above.

In a fourth aspect, a method for manufacturing the scintillation crystal array as described above is provided, comprising:

arranging the first reflecting layers in a part of the gaps of the scintillation crystal array, and arranging the second reflecting layers in a part of the gaps, wherein the first reflecting layers are made of a thin film-like material, and the second reflecting layers are made of an amorphous material In the embodiment of the application, a combination of the first and second reflecting layers is used to fill the gaps between the scintillation crystal units, the first reflecting layers are made of a thin film material with high reflectivity, the second reflecting layers are made of an amorphous material which has fluidity or plasticity, and together, they can fill the gaps at the intersection positions. In this way, it is possible to leverage the high reflectivity of the thin film-like material in the scintillation crystal array while effectively preventing light leakage or crosstalk issues at the intersection positions, thus improving PET image quality and avoiding image distortion. Moreover, during the flattening of the second reflecting layers, the first reflecting layers remain stable and free from misalignment and deformation, thereby ensuring uniform thickness of the reflecting layers and uniform distribution of the scintillation crystal units. This enables clear differentiation after decoding of PET images obtained. The scintillation crystal array according to the embodiment of the application successfully eliminates light leakage or crosstalk issues in the reflecting layers, while also reducing processing complexity and ensuring product accuracy. Thus, light collection efficiency is effectively enhanced, detector performance is improved, and PET imaging quality is higher.

DETAILED DESCRIPTION OF EMBODIMENTS

The technical schemes in the embodiments of the application will be clearly described below in combination with attached drawings. Obviously, the described embodiments are part of the embodiments of the application, not all of them. Based on the embodiments of the application, all other embodiments obtained by those of ordinary skill in the art belong to the scope of the application.

The terms "first" and "second" in the specification and claims of this application are used to distinguish similar objects, and are not used to describe a specific order or sequence. It should be understood that the data used in this way can be interchanged under appropriate circumstances, so that the embodiments of the application can be implemented in an order other than those illustrated or described here. The objects distinguished by "first" and "second" are usually of the same type, and the number of objects is not limited, for example, there may be one or more first objects. In addition, the usage of "and/or" between objects in the specification and claims implies the inclusion of at least one of the connected objects, and the "/" character typically denotes an "or" relationship between the associated objects.

In order to better understand the application, PET and related contents will be briefly described first.

Figure 10:
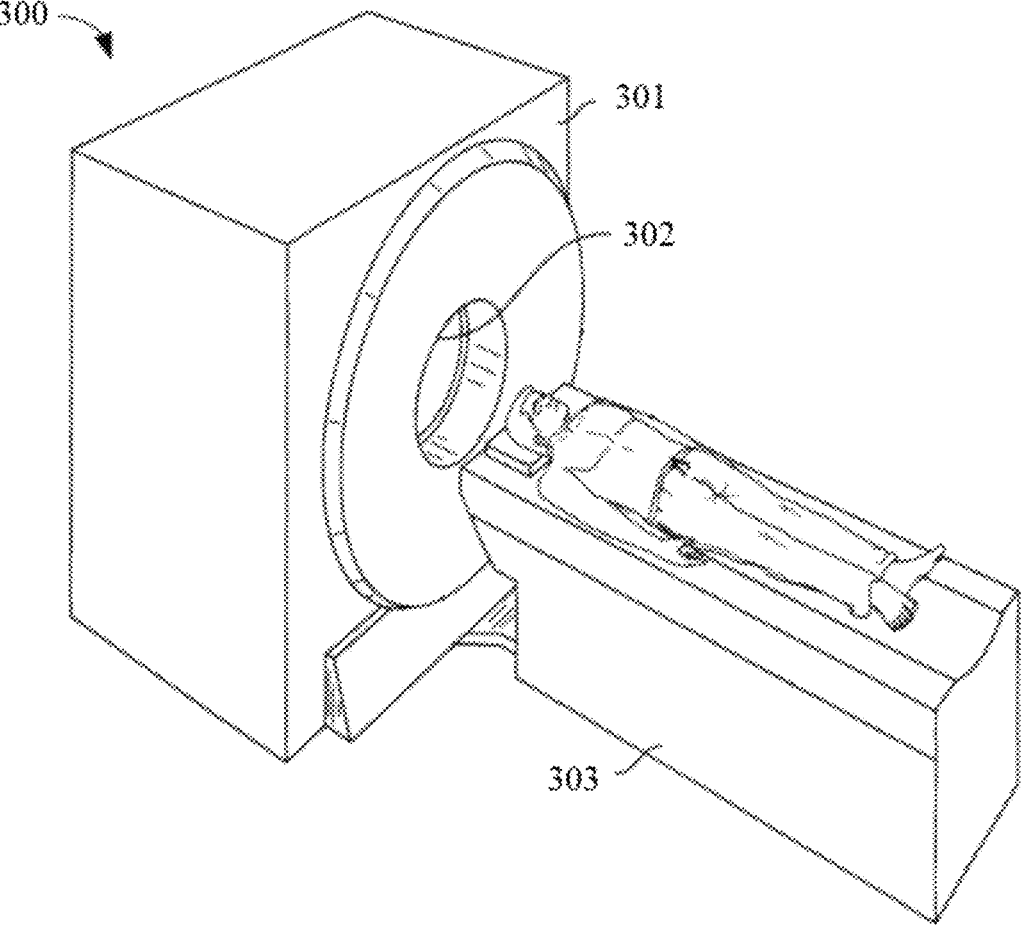
FIG. 10 is a structural diagram of a PET system.
Figure 11:
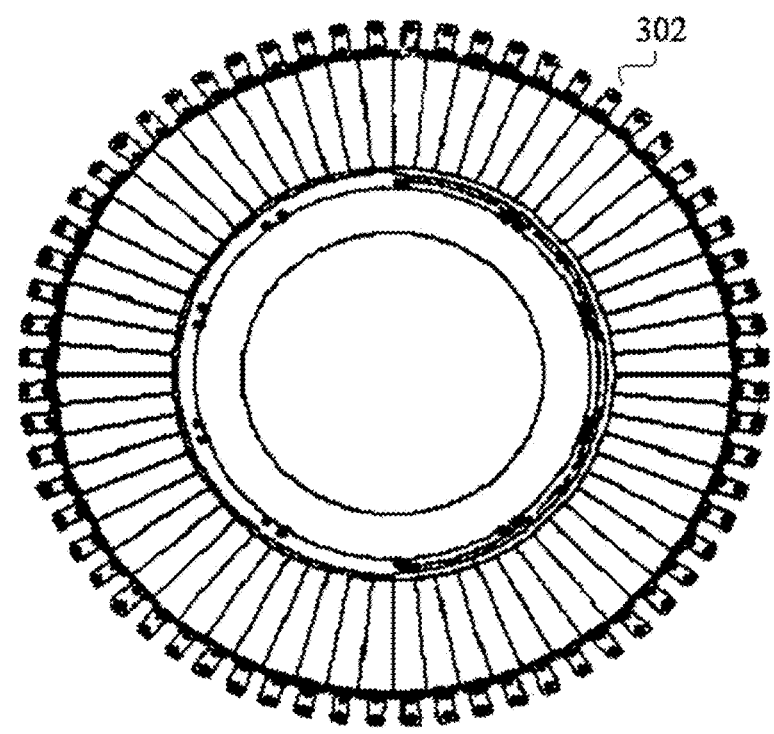
FIG. 11 is a structural diagram of a detector ring.

As shown in FIGS. 10 and 11, a PET system 300 comprises a main unit 301 and a bed 303. The main unit 301 is provided with a detector ring 302 which includes several detectors, and a detected object can enter the detector ring 302 with the bed 303. Each detector comprises a scintillation crystal array, a photoelectric sensor and a post-processing circuit. Here, the photoelectric sensor can be, for example, a photomultiplier tube (PMT) or a silicon photomultiplier (SiPM). The scintillation crystal array can receive photons emitted from the detected object and convert them into optical signals, the photoelectric sensor converts the optical signals into readable electrical signals, and the post-processing circuit performs imaging based on the electrical signals.

Scintillation crystal array assembly is the core technology of PET. The uniformity of distribution of units in the scintillation crystal array and the consistency of alignment in the X/Y directions on a two-dimensional plane have a direct impact on the coupling quality of a detector module and the detection efficiency of the detector. At present, the resolution of most commercially available ultra-precise PET systems is below 2 mm, which limits the size of crystal units in the scintillation crystal array, thus raising higher demands on array production.

Figure 12:
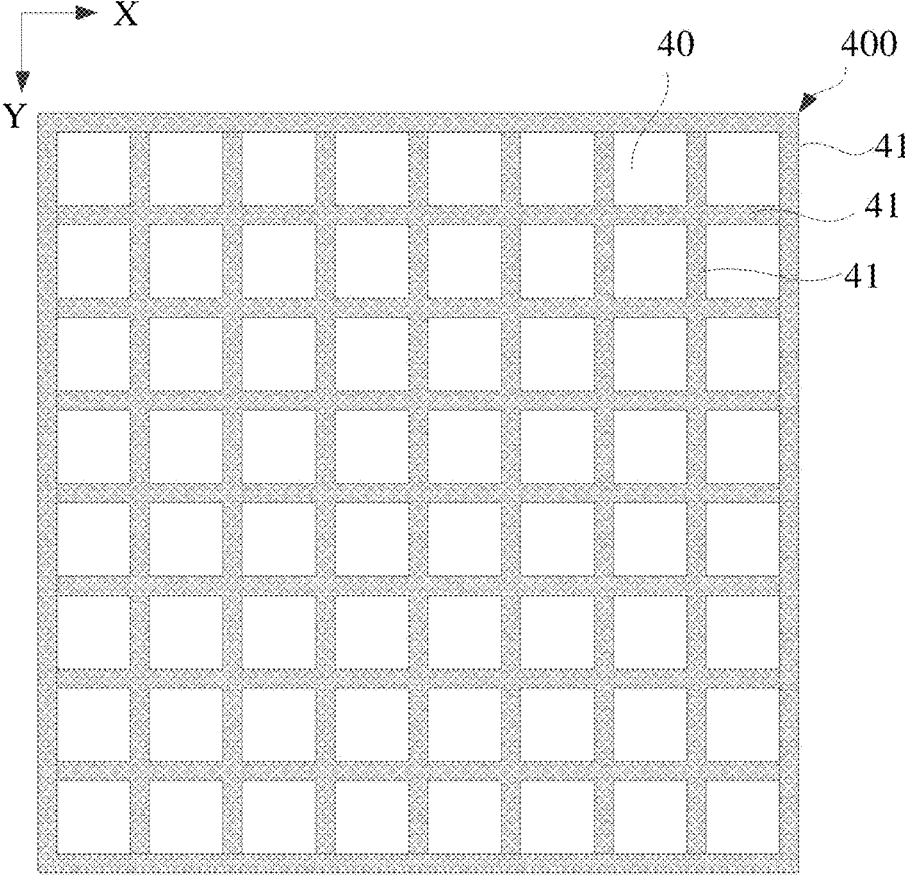
FIG. 12 is a schematic diagram of an existing scintillation crystal array using barium sulfate reflecting layers.
Figure 16:
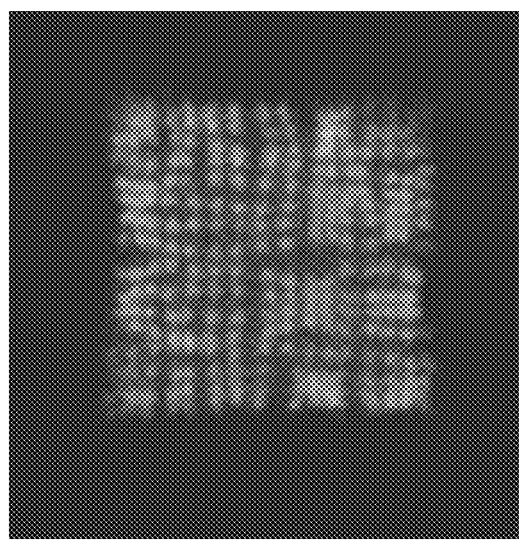
FIG. 16 is a scatter diagram of test results for the application of an existing scintillation crystal array using barium sulfate reflecting layers to PET.

In a scintillation crystal array 400 shown in FIG. 12, gaps between scintillation crystal units 40 are filled with barium sulfate reflecting layers 41. The barium sulfate reflecting layer 41 is generally a resin material doped with barium sulfate powder. In the manufacturing process of the scintillation crystal array 400, after the scintillation crystal units 40 are arranged, the flowing barium sulfate reflecting layers 41 are injected between the scintillation crystal units 40, and then the barium sulfate reflecting layers 41 are flattened manually or with the aid of auxiliary tools, and then allowed to solidify. The inventors found that because the barium sulfate reflecting layer 41 has fluidity or plasticity in the manufacturing process, compression in one direction (for example, X direction) may cause misalignment or deformation in the other direction (Y direction), making it difficult to ensure consistent thickness and consistent alignment in the X/Y directions, thus resulting in non-uniform distribution of the crystal units. Therefore, when the barium sulfate reflecting layers 41 are used to manufacture scintillation crystal arrays, especially ultra-small scintillation crystal arrays, there are problems such as complicated operation, great processing difficulty, poor processing accuracy, and non-uniform distribution of scintillation crystal units. As shown in FIG. 16, when the scintillation crystal array 400 using the barium sulfate reflecting layers 41 is installed in a PET device for image testing, the non-uniform distribution of the scintillation crystal units leads to unclear differentiation in PET image decoding, with some pixels having significant gaps and others being stuck together due to compression.

Figure 13:
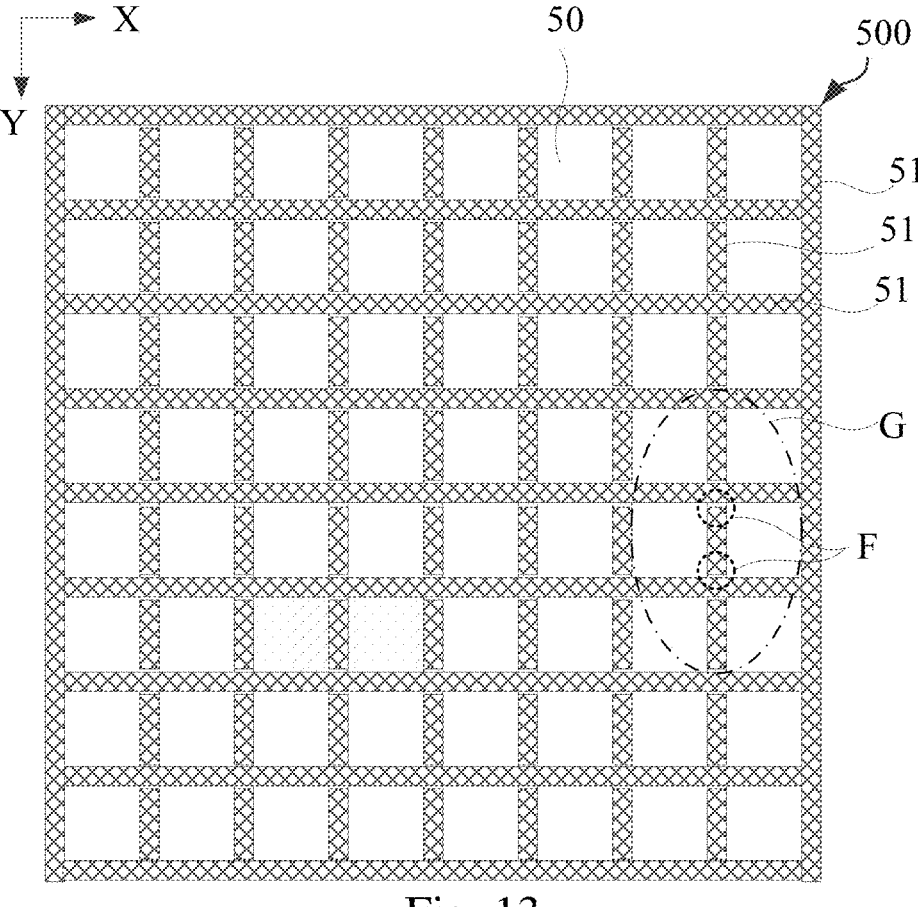
FIG. 13 is a schematic diagram of an existing scintillation crystal array using ESR reflecting layers.

In order to solve the problem that the barium sulfate reflecting layers are difficult to process and the scintillation crystal units are unevenly distributed, the inventor uses a scintillation crystal array 500 as shown in FIG. 13, where gaps between scintillation crystal units 50 are filled with thin film-like ESR reflecting layers 51, which have no fluidity or plasticity so as to ensure uniform thickness in X and Y directions, and are easy to process. Moreover, the reflectivity of the ESR reflecting layer 51 is as high as 98%. In general human PET applications, scintillation crystal arrays 500 using the ESR reflecting layer 51 show excellent performance, as it enables more scintillation light to be reflected and collected by optical detectors, which improves the signal-to-noise ratio and detector efficiency. However, the inventors have discovered that when the ESR layer 51 is applied to ultra-small scintillation crystal arrays (0.5 mm), it not only fails to exhibit the advantage of high reflectivity but also results in significant distortion in PET images.

Figure 14:
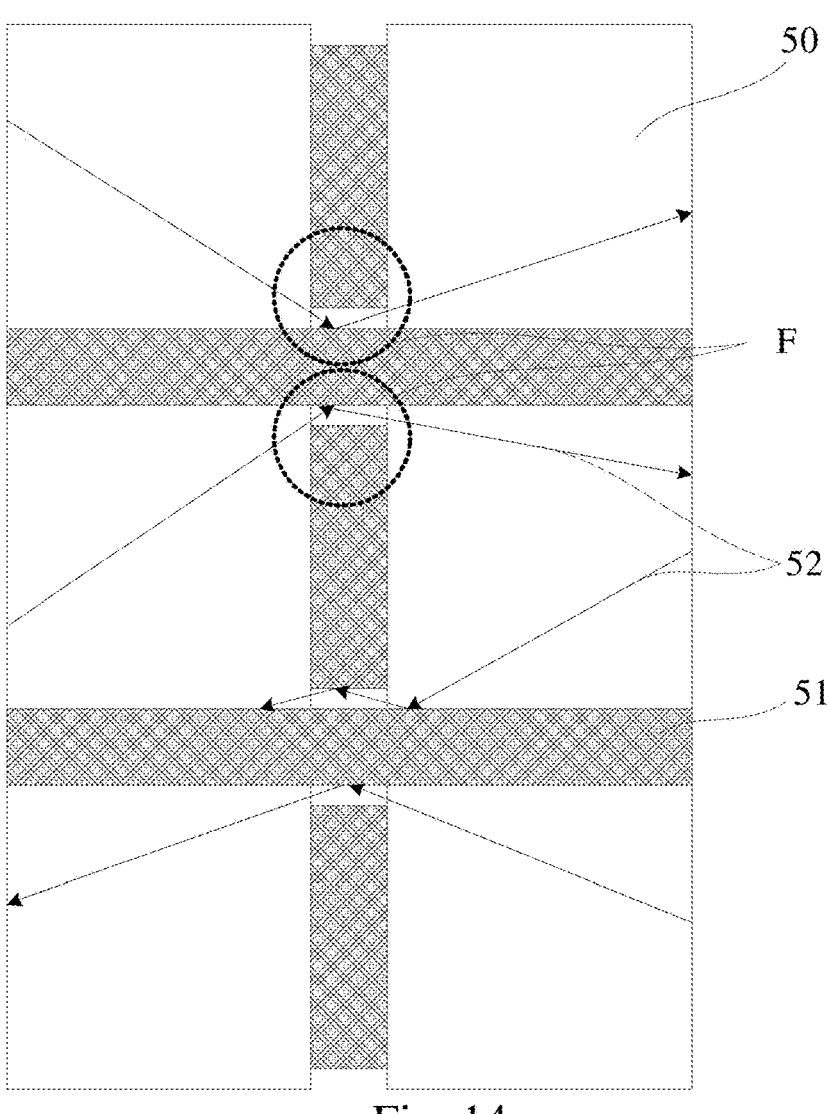
FIG. 14 is a schematic diagram of light inside an area G in FIG. 13.
Figure 15:
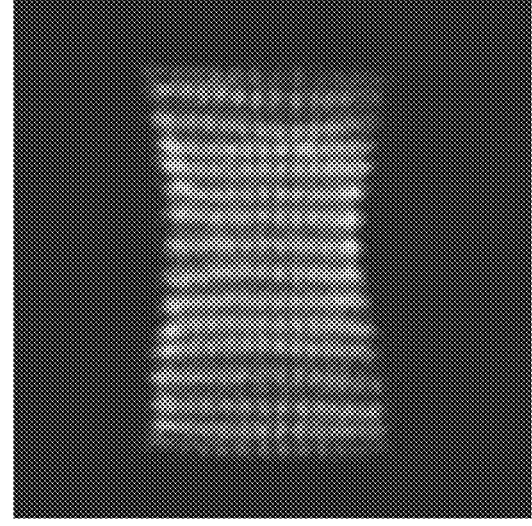
FIG. 15 is a scatter diagram of test results for the application of an existing scintillation crystal array using ESR reflecting layers to PET.

After repeated research, the inventors found that the cause of PET image distortion is when the thin film-like ESR reflecting layers 51 are filled between the crystals in approximately perpendicular directions (X direction and Y direction), the ESR reflecting layers 51 in at least one direction at an intersection position F of the gaps between two crystals are disconnected or discontinuous. As shown in FIG. 14, scintillation light of the scintillation crystal units 50 will cross-talk to the adjacent crystal units through the intersection position F, which will affect the performance of the detector and the quality of PET imaging. This light leakage phenomenon is more obvious when the scintillation crystal unit is small (0.5 mm), because the smaller the scintillation crystal unit, the larger the ratio of a notch of the reflecting layer to the total area of the reflecting layer, resulting in a higher proportion of light leakage, which is unacceptable for ultra-precise PET using an ultra-small scintillation crystal array. As shown in FIG. 15, when a square scintillation crystal array 500 using ESR reflecting layers 51 is installed in an ultra-precise PET device for image testing, according to application requirements, the aspect ratio of a scatter diagram should correspond to the aspect ratio of the scintillation crystal array 500. However, due to the light leakage or crosstalk at the fracture position of the ESR thin film, the scatter diagram is rectangular, and the image is distorted (compressed in the X direction), which affects the imaging effect.

In this technical field, it is an arduous challenge to overcome the difficulty in processing barium sulfate, give full play to the advantages of high reflectivity thin film materials represented by ESR thin film reflecting layers, and at the same time overcome the shortcomings of light leakage or crosstalk to meet the high-precision application requirements of ultra-precise PET. The main difficulty lies in innovative thinking for improvement strategies and finding feasible solutions for practical operations.

Based on the above research, an embodiment of the application proposes a scintillation crystal array with mixed reflecting layers. Specifically, a combination of first and second reflecting layers is used to fill the gaps between the scintillation crystal units, the first reflecting layers are made of a thin film material with high reflectivity, the second reflecting layers are made of an amorphous material (having no definite shape) which has fluidity or plasticity, and together, they can fill the gaps at the intersection positions. In this way, it is possible to leverage the high reflectivity of the thin film-like material in the scintillation crystal array while effectively preventing light leakage or crosstalk issues at the intersection positions, thus improving PET image quality and avoiding image distortion. Moreover, during the flattening of the second reflecting layers, the first reflecting layers remain stable and free from misalignment and deformation, thereby ensuring uniform thickness of the reflecting layers and uniform distribution of the scintillation crystal units. This enables clear differentiation after decoding of PET images obtained. The scintillation crystal array according to the embodiment of the application successfully eliminates light leakage or crosstalk issues in the reflecting layers, while also reducing processing complexity and ensuring product accuracy. Thus, light collection efficiency is effectively enhanced, detector performance is improved, and PET imaging quality is higher.

FIG. 1A-8 are schematic diagrams of exemplary scintillation crystal arrays according to some embodiments of the application. As shown in FIG. 1A-8, the scintillation crystal array 100 comprises a plurality of scintillation crystal units 10, a gap is provided between each two adjacent scintillation crystal units 10, first reflecting layers 31 are arranged in a part of the gaps 20 of the scintillation crystal array 100, and second reflecting layers 32 are arranged in a part of the gaps 20.

The first reflecting layers 31 are made of a thin film-like material, which have a stable shape and high reflectivity, and are not easily deformed in the process of manufacturing the scintillation crystal array. The second reflecting layers 32 are made of an amorphous material, and their inherent fluidity or plasticity enables them to fill the gaps at the intersection positions, effectively eliminating light leakage or crosstalk issues.

Figure 17:
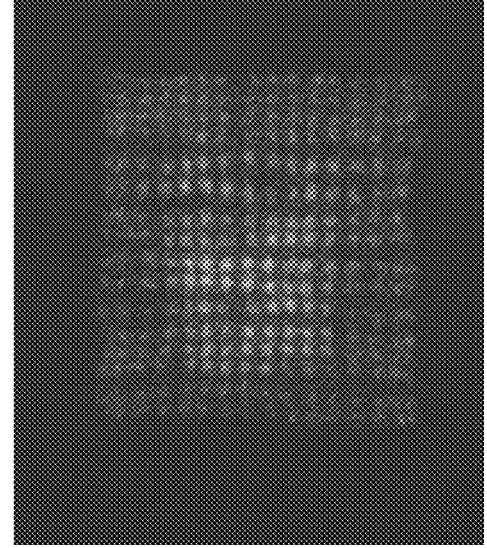
FIG. 17 is a scatter diagram of test results for the application of a scintillation crystal array provided by an embodiment of the application to PET.

In this way, by filling the gaps 20 between the scintillation crystal units 10 with the combination of the first reflecting layers 31 and the second reflecting layer 32, it is possible to leverage the high reflectivity of the thin film-like material while effectively preventing light leakage or crosstalk issues in the scintillation crystal array, thereby improving the light collection efficiency of a detector including the scintillation crystal array, preventing PET image distortion in detector applications, and improving detector performance and PET imaging quality. Moreover, during the flattening of the second reflecting layers 32, the first reflecting layers 31 remain stable and free from misalignment and deformation, thereby ensuring uniform thickness of the reflecting layers and uniform distribution of the scintillation crystal units 10. This enables clear differentiation after decoding of PET images obtained. Especially for ultra-small scintillation crystal arrays, by the combination of the first reflecting layers 31 and the second reflecting layers 32, ultra-high precision light collection efficiency can be achieved to support ultra-precise PET imaging. As shown in FIG. 17, when the scintillation crystal array 100 using a mixture of the two reflecting layers is installed in a PET device for image testing, the scatter diagram exhibits consistent X and Y axis scaling without any distortion. Moreover, decoded spots are clear and uniform, enabling the differentiation of each point and allowing for normal use on the PET device.

Figure 2:
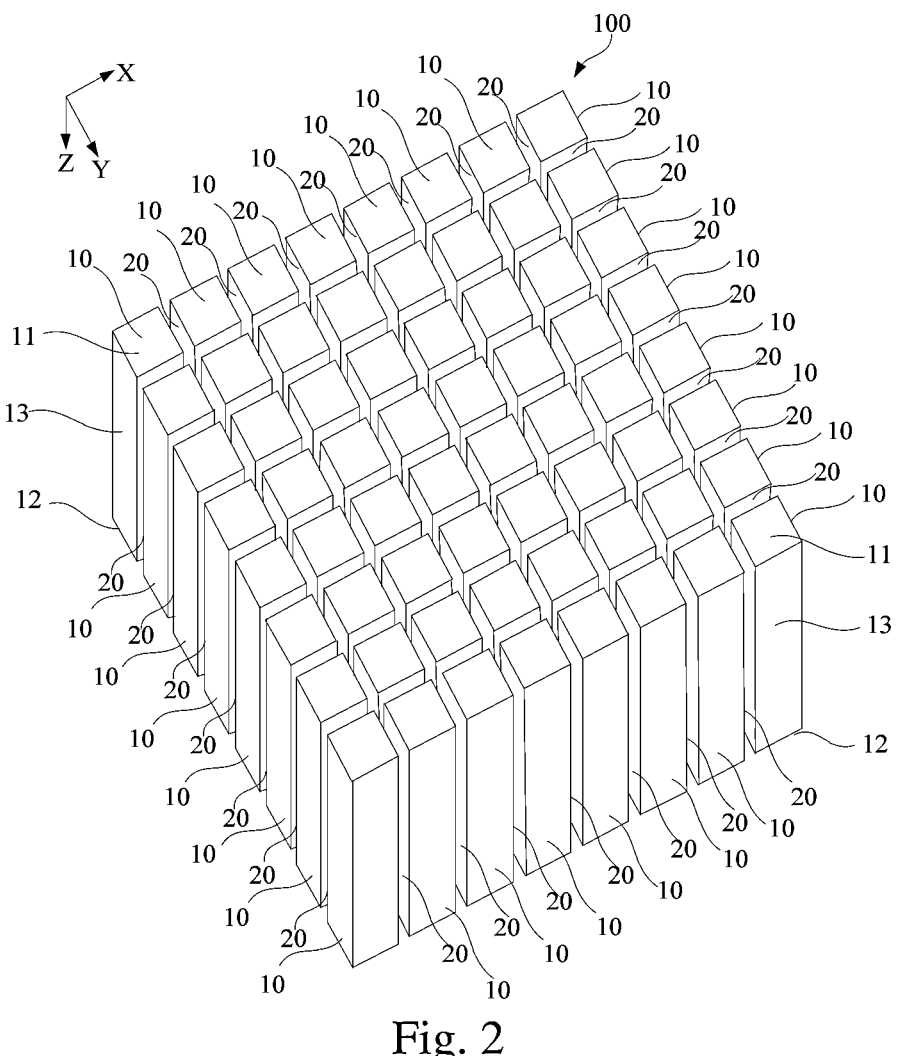
FIG. 2 is a schematic diagram showing the arrangement of exemplary scintillation crystal units according to an embodiment of the application.

In some embodiments, as shown in FIG. 2, the plurality of scintillation crystal units 10 can be arranged into a plurality of rows (for example, M rows) in a first direction (for example, X direction) and into a plurality of columns (for example, N columns) in a second direction (for example, Y direction). The first direction is approximately perpendicular to the second direction. Here, M and N can be the same or different, for example, both M and N are 8, or M is 6 and N is 5. The sizes of the scintillation crystal units 10 may be the same or different. The shape of the scintillation crystal units 10 can be, for example, a rectangular prism, a cube, etc., which is not limited thereto.

Figure 3:
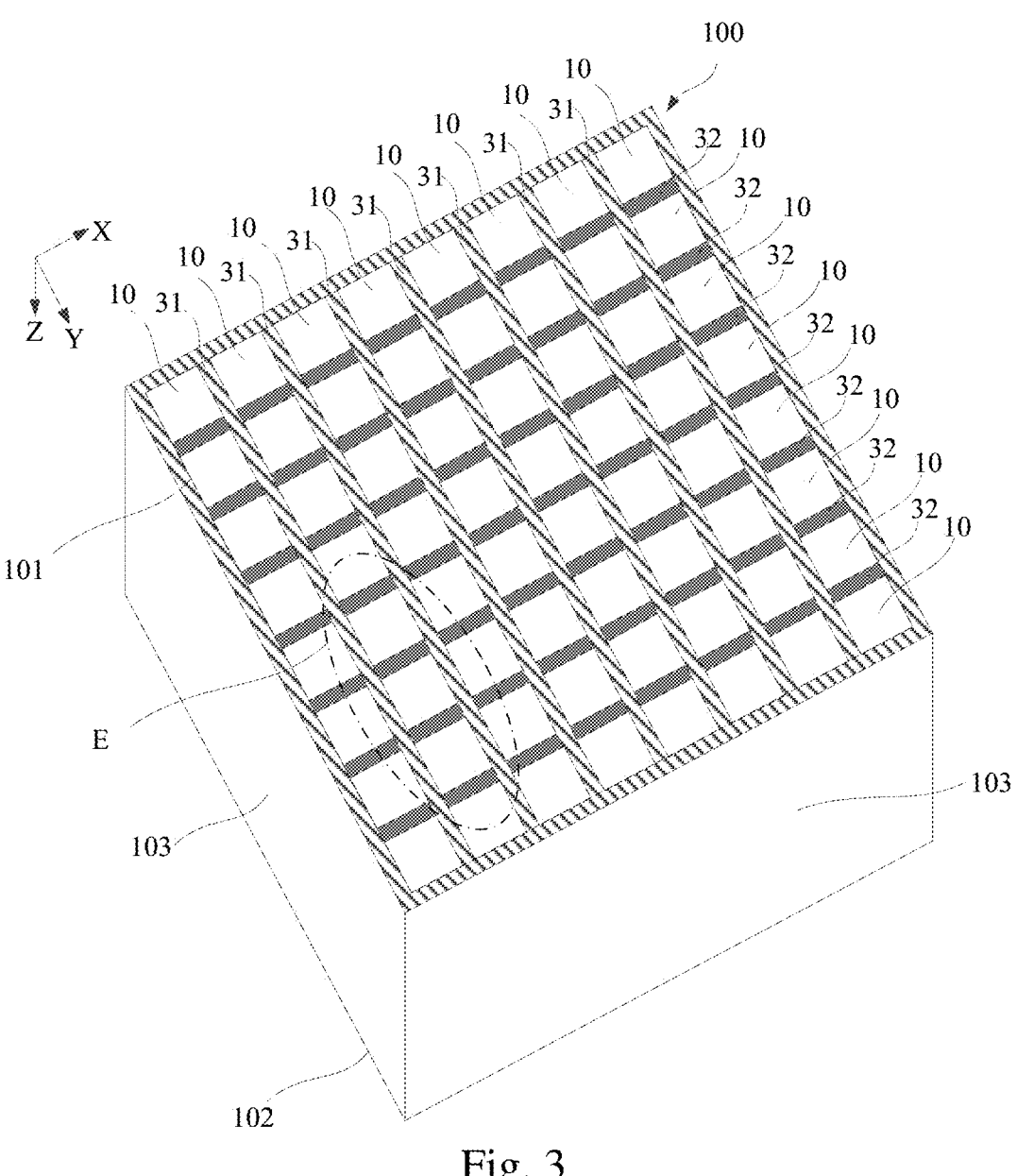
FIG. 3 is a perspective view of an exemplary scintillation crystal array provided by an embodiment of the application.

In some embodiments, as shown in FIGS. 2 and 3, each scintillation crystal unit 10 may comprise a top surface 11, a bottom surface 12 opposite to the top surface 11, and side surfaces 13 extending between the top surface 11 and the bottom surface 12. After the scintillation crystal units 10 are arranged into the scintillation crystal array 100, the top surfaces 11 of all the scintillation crystal units 10 face one side as a light-emitting surface 101, and the bottom surfaces 12 of all the scintillation crystal units 10 face one side as an incident surface 102. In practical application, the incident surface 102 of the scintillation crystal array 100 faces a tested object, and the light-emitting surface 101 is connected with a photoelectric sensor. Radiant energy emitted from the tested object enters the scintillation crystal array 100 from the incident surface 102, and is converted into optical signals by the scintillation crystal array 100. The optical signals generated by the scintillation crystal array 100 are emitted from the light-emitting surface 101 and reach the photoelectric sensor, which converts the optical signals into readable electrical signals. Gaps 20 are arranged between inner side surfaces of any two adjacent scintillation crystal units 10 for accommodating the reflecting layers, so as to prevent optical crosstalk between adjacent scintillation crystal units 10.

Figure 9:
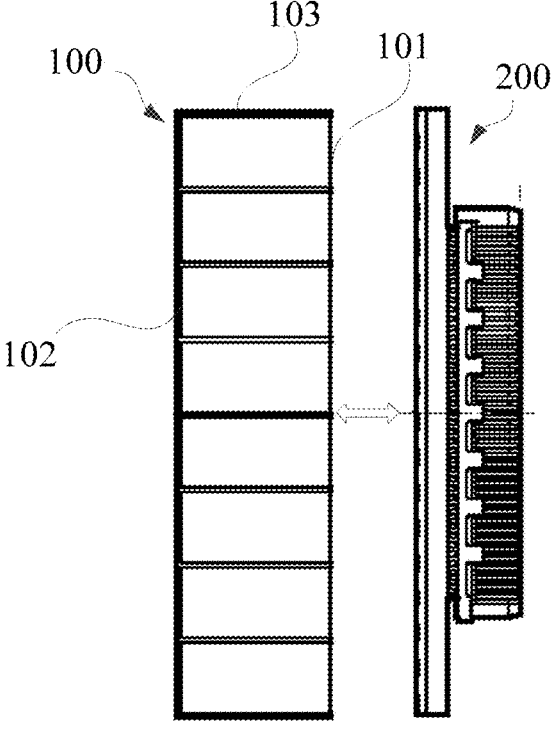
FIG. 9 is a perspective view of an exemplary detector provided by an embodiment of the application.

In some embodiments, as shown in FIG. 9, the light-emitting surface 101 of the scintillation crystal array 100 can be connected with an SiPM array 200, the optical signals emitted by the scintillation crystal units 10 of the scintillation crystal array 100 are collected and converted into electrical signals by SiPM units on the SiPM array 200, and imaging is performed based on the electrical signals of the SiPM array 200.

In some embodiments, the thickness of the gaps 20 between the scintillation crystal units 10 may be greater than or equal to 0.01 mm and less than or equal to 0.5 mm.

In some embodiments, side surfaces of the scintillation crystal unit 10 can be divided into an inner side surface facing the inside of the array and an outer side surface facing the outside of the array, and the outer side surfaces of the plurality of scintillation crystal units 10 constitute an outer side surface 103 of the scintillation crystal array 100. The outer side surface 103 and the incident surface 102 of the scintillation crystal array also need to be provided with reflecting layers to ensure that all scintillation light is output from the light-emitting surface 101 and reaches the photoelectric sensor. In some embodiments, the reflecting layer on the outer side surface 103 and the reflecting layer on the incident surface 102 of the scintillation crystal array 100 may be the same or different. For example, the reflecting layers on the outer side surface 103 and the incident surface 102 of the scintillation crystal array 100 may be thin film reflecting layers such as ESR with high reflectivity, which is not limited thereto.

In some embodiments, the top surface 11 of each scintillation crystal unit 10 may be smooth, and the bottom surface 12 and the side surfaces 13 of each scintillation crystal unit 10 may be smooth or rough.

In some embodiments, the scintillation crystal unit 10 may be made from NaI (Tl), CsI (Tl), CWO, BGO, LYSO, GAGG, RGBS, etc., which is not limited thereto.

In some embodiments, the first reflecting layers 31 can be selected from one or more of: ESR reflecting layers, polyethylene terephthalate reflecting layers, polytetrafluoroethylene film reflecting layers, aluminum foil reflecting layers and aluminum-plated plastic reflecting layers.

Here, the ESR reflecting layer is a typical high-reflectivity thin film reflecting material, and the first reflecting layer 31 can be an ESR reflecting layer so as to improve the light collection efficiency, or a polyethylene terephthalate (PET) reflecting layer, a polytetrafluoroethylene film, aluminum foil, an aluminum-plated plastic film and the like. The reflectivity of thin film reflecting layers such as ESR can reach 90% or more.

In some embodiments, the second reflecting layers 32 can be selected from one or more of: reflecting layers made of powder materials, reflecting layers made of liquid materials, reflecting layers made of a mixture of powder materials and liquid materials, and reflecting layers made of paste materials.

Here, powder materials, liquid materials, a mixture of powder materials and liquid materials, and paste materials all have fluidity or plasticity, and can fill the gaps at the intersection positions, effectively eliminating light leakage or crosstalk issues of crystals.

It should be noted that the fluidity or plasticity of the second reflecting layer 32 refers to the state at a certain stage in the manufacturing process, and finally the second reflecting layer 32 will become a reflecting layer with a stable state after pressing and solidification. For example, in a case where the second reflecting layer 32 is a made of a powder material and a liquid material, during manufacturing, a mixture of the powder material and the liquid material is filled in the gaps 20 between the scintillation crystal units 10 and the gaps at the intersection positions, and after solidification, a reflecting layer with a stable state is formed.

In some embodiments, the second reflecting layers 32 can be selected from one or more of: barium sulfate reflecting layers, titanium dioxide reflecting layers, magnesium oxide reflecting layers and polytetrafluoroethylene powder reflecting layers.

Here, the barium sulfate reflecting layer, the titanium dioxide reflecting layer, the magnesium oxide reflecting layer and the polytetrafluoroethylene powder reflecting layer can be reflecting layers formed by doping inorganic compound powders such as barium sulfate, titanium dioxide, magnesium oxide and polytetrafluoroethylene into organic resin. These reflecting layers have fluidity during manufacture and form reflecting layers with a stable form after solidification. In some embodiments, the organic resin may be epoxy resin, acrylic resin, phenol resin, etc.

In some embodiments, the scintillation crystal array 100 comprises first gaps 21 arranged in a first direction and second gaps 22 arranged in a second direction; and Here, the first direction can be the X direction, the second direction can be the Y direction, and the first direction is approximately perpendicular to the second direction. If the first gap 21 and the second gap 22 arranged in two directions intersect, it is necessary to ensure that there is no gap at the intersection position.

Figures 4, 5:
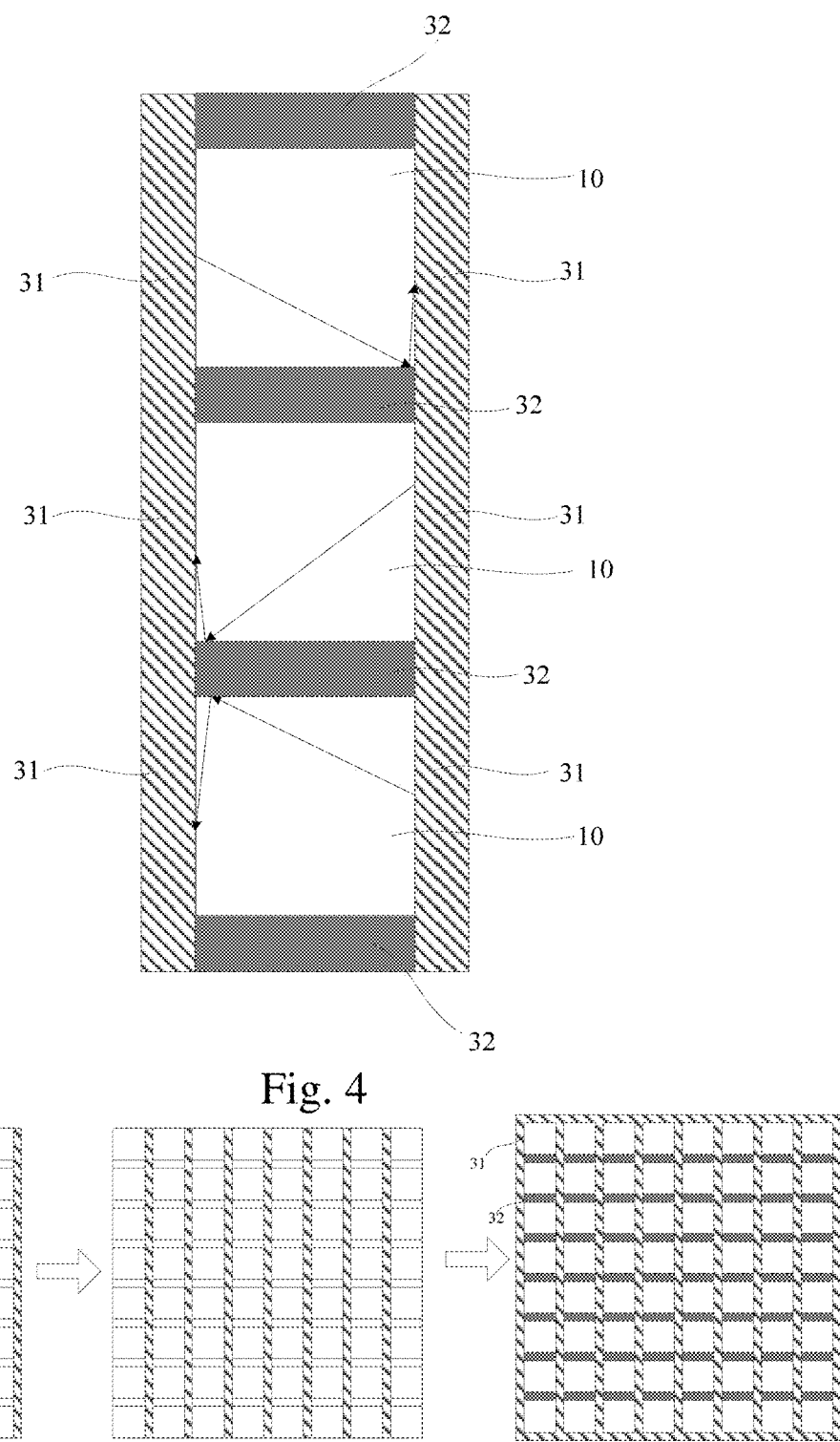
FIG. 4 is a schematic diagram of light inside an area E in FIG. 3.
FIG. 5 is a schematic diagram showing the manufacturing of an exemplary scintillation crystal array provided by an embodiment of the application.

Specifically, the first reflecting layers 31 and the second reflecting layers 32 can be arranged in part of or all intersecting first gaps 21 and second gaps 22, so as to solve the problem of light leakage or crosstalk at the intersection positions. As shown in FIG. 4, by filling the gaps 20 that intersect perpendicularly with the two kinds of reflecting layers, the gaps at the intersection positions can be filled with the second reflecting layers 32, so even if light is incident at the intersection positions, there will be no crosstalk to other scintillation crystal units 10 or light leakage.

Figure 7:
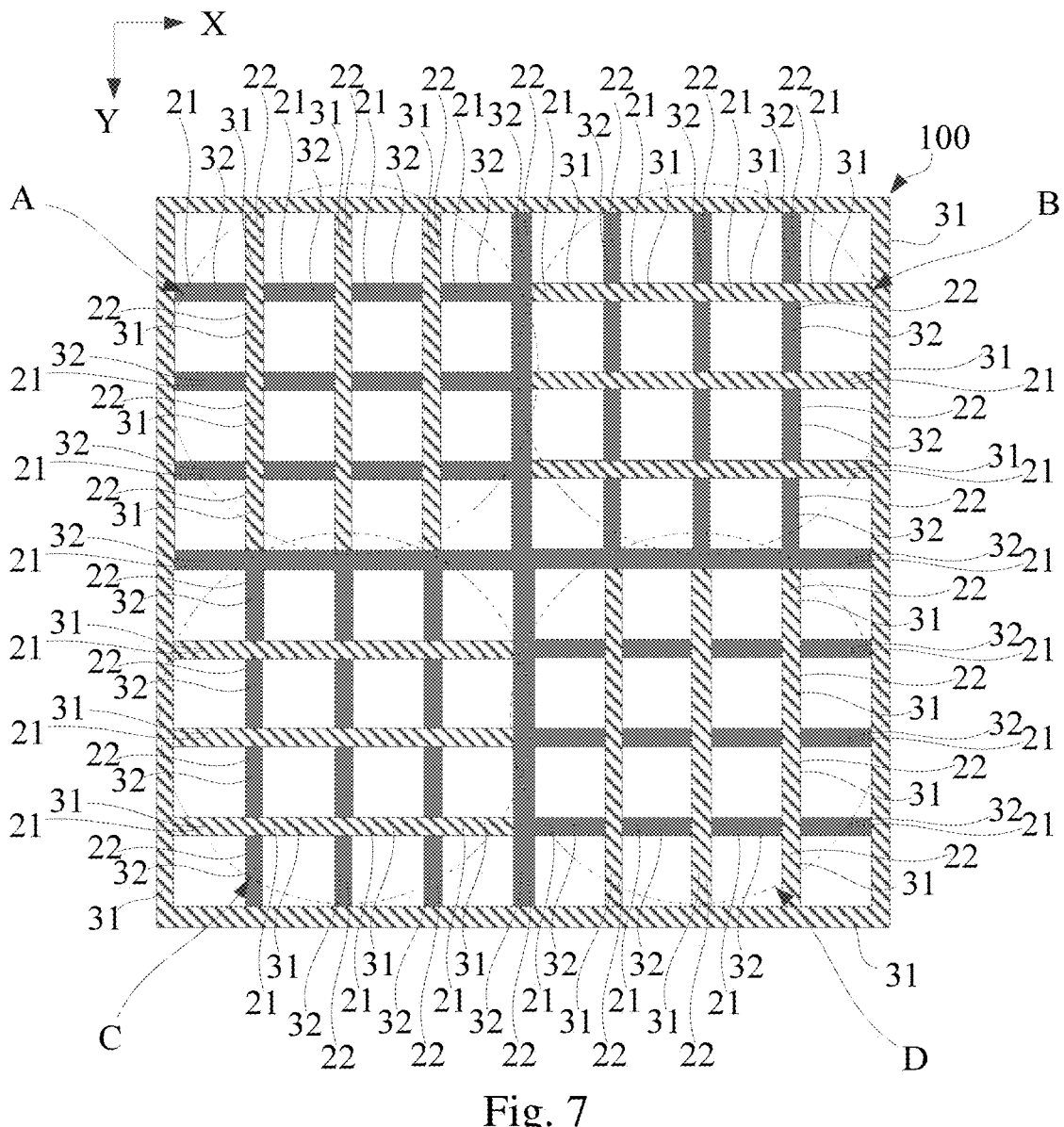
FIG. 7 is a top view of another exemplary scintillation crystal array provided by an embodiment of the application.
Figure 8:
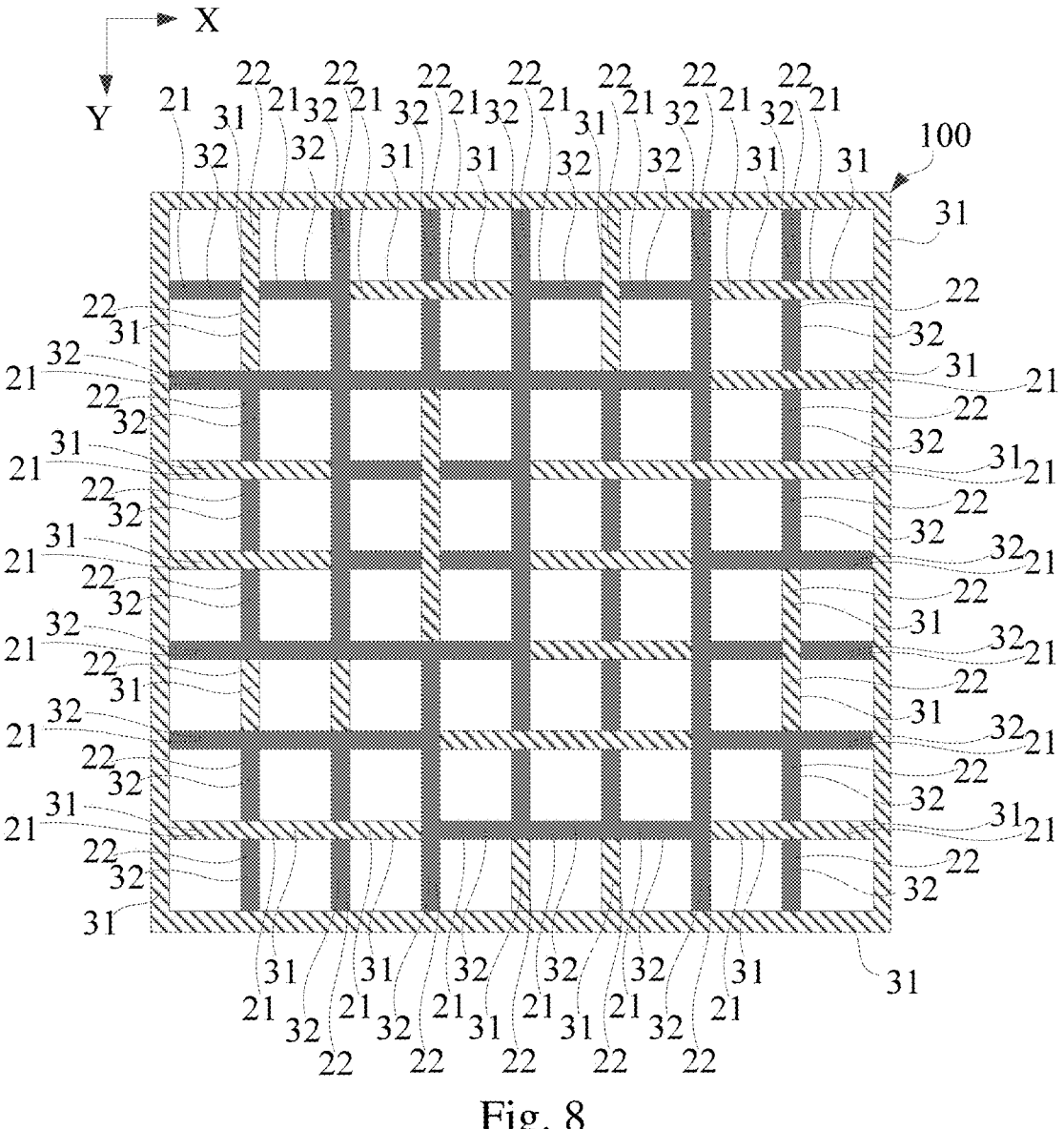
FIG. 8 is a top view of yet another exemplary scintillation crystal array provided by an embodiment of the application.

As an alternative implementation, as shown in FIGS. 7 and 8, a part of intersecting first gaps 21 and second gaps 22 in the scintillation crystal array 100 are respectively provided with the first reflecting layers 31 and the second reflecting layers 32.

In this case, by filling part of the gaps 20 that intersect perpendicularly with the two kinds of reflecting layers, the gaps at most of the intersection positions can be filled with the second reflecting layers 32, so as to avoid light leakage or crosstalk at the intersection positions, improve the light collection efficiency of the detector including the scintillation crystal array, prevent PET image distortion when the detector is applied to PET, and improve detector performance and PET imaging quality. Moreover, the first reflecting layer 31 in the first gap 21 has stability, which can avoid deformation when the second reflecting layer 32 in the other direction is compressed, thus ensuring uniform thickness of the final reflecting layer obtained after compression. As a result, the scintillation crystal units 10 are uniformly distributed, and clear differentiation is realized after decoding of PET images obtained.

In a case where a part of intersecting first gaps 21 and second gaps 22 in the scintillation crystal array 100 are respectively provided with the first reflecting layers 31 and the second reflecting layers 32, in order to further improve the light collection efficiency, optionally, the second reflecting layers 32 are arranged in gaps 20 in the scintillation crystal array 100 except the said part of intersecting first gaps 21 and second gaps 22.

In this case, by filling part of the gaps 20 that intersect perpendicularly with the two kinds of reflecting layers and the remaining gaps 20 with the second reflecting layers 32, light leakage or crosstalk in the remaining gaps 20 can be avoided, so as to ensure that there is no light leakage or crosstalk in the whole scintillation crystal array 100, which further improves the light collection efficiency.

Although the above scheme where part of the gaps 20 that intersect perpendicularly are filled with the two kinds of reflecting layers and the remaining gaps 20 are filled with the second reflecting layers 32 can ensure that there is no light leakage or crosstalk in the whole scintillation crystal array 100, there is still room for improvement in light collection efficiency.

In order to further improve the light collection efficiency, as shown in FIGS. 1A-1D and FIG. 3, as another alternative implementation, all intersecting first gaps 21 and second gaps 22 in the scintillation crystal array 100 are respectively provided with the first reflecting layers 31 and the second reflecting layers 32.

In this case, by filling all intersecting first gaps 21 and second gaps 22 with the two kinds of reflecting layers, the gaps at all the intersection positions in the array can be filled by means of the fluidity and plasticity of the second reflecting layers 32, which ensures that there is no light leakage or crosstalk in the whole array; and by increasing the use ratio of the first reflecting layers 31 in the array, the high reflectivity of the thin film material can be effectively utilized, so as to further improve the light collection efficiency of the detector including the scintillation crystal array, prevent PET image distortion when the detector is applied to PET, and improve detector performance and PET imaging quality. Moreover, the overall structure is more stable, and deformation can be can avoided when the second reflecting layer 32 in the other direction is compressed, thus ensuring uniform thickness of the final reflecting layer obtained after compression. As a result, the scintillation crystal units 10 are uniformly distributed, and clear differentiation is realized after decoding of PET images obtained.

For the above schemes where part of or all intersecting first gaps 21 and second gaps 22 are filled with the two kinds of reflecting layers, the distribution of the two kinds of reflecting layers in the array can be regular, as shown in FIGS. 1A-1D and FIG. 7, or irregular (multiple variations are possible), as shown in FIG. 8. However, in order to improve the stability of the whole structure and reduce processing difficulty, the regular distribution mode is optimized.

Preferably, in the first gaps 21 and the second gaps 22 respectively provided with the first reflecting layers 31 and the second reflecting layers 32, all the first gaps 21 are provided with the first reflecting layers 31 and all the second gaps 22 are provided with the second reflecting layers 32, or all the first gaps 21 are provided with the second reflecting layers 32 and all the second gaps 22 are provided with the first reflecting layers 31.

Figure 1A:
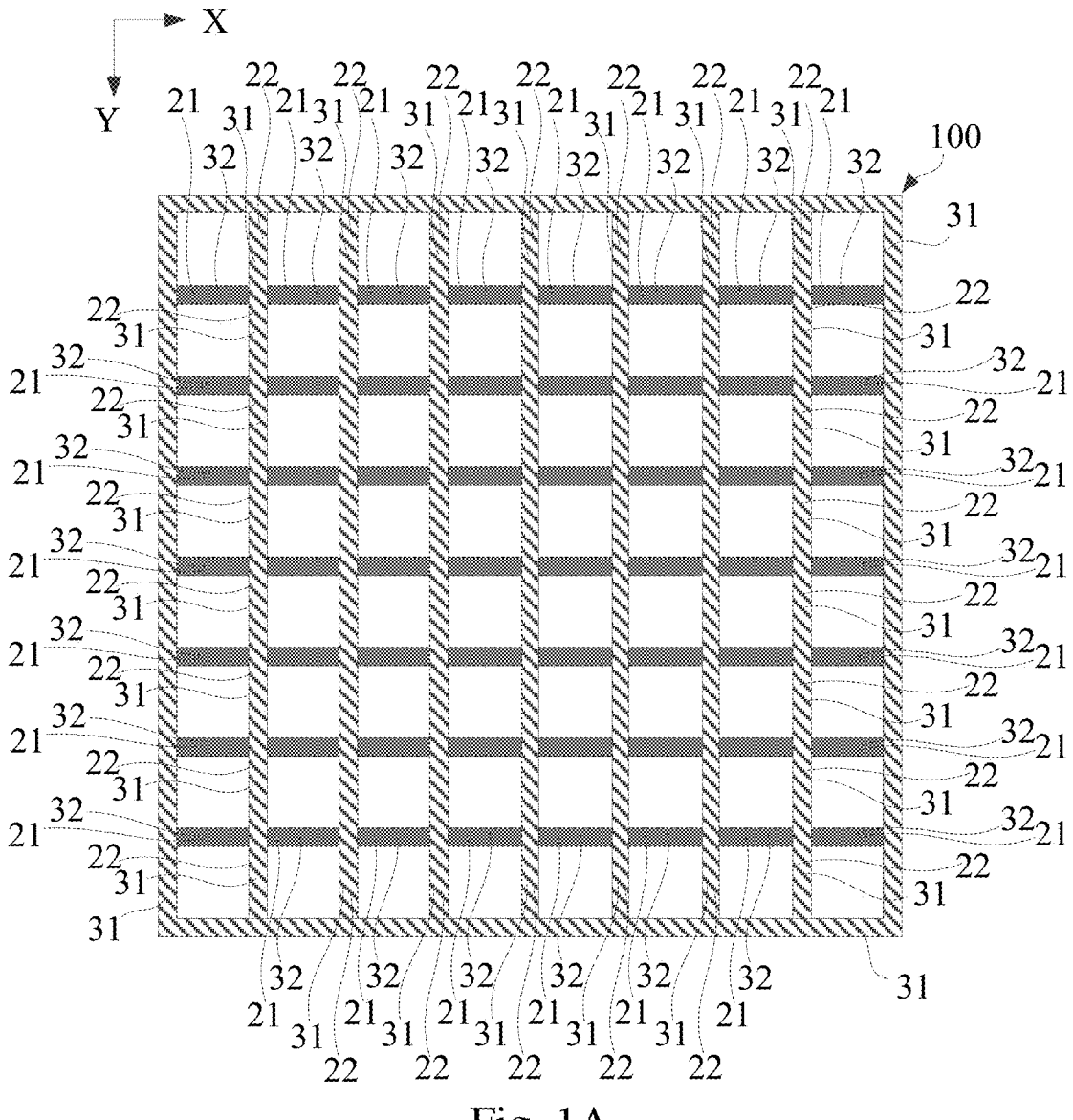
FIG. 1A is a top view of an exemplary scintillation crystal array provided by an embodiment of the application.
Figure 1B:
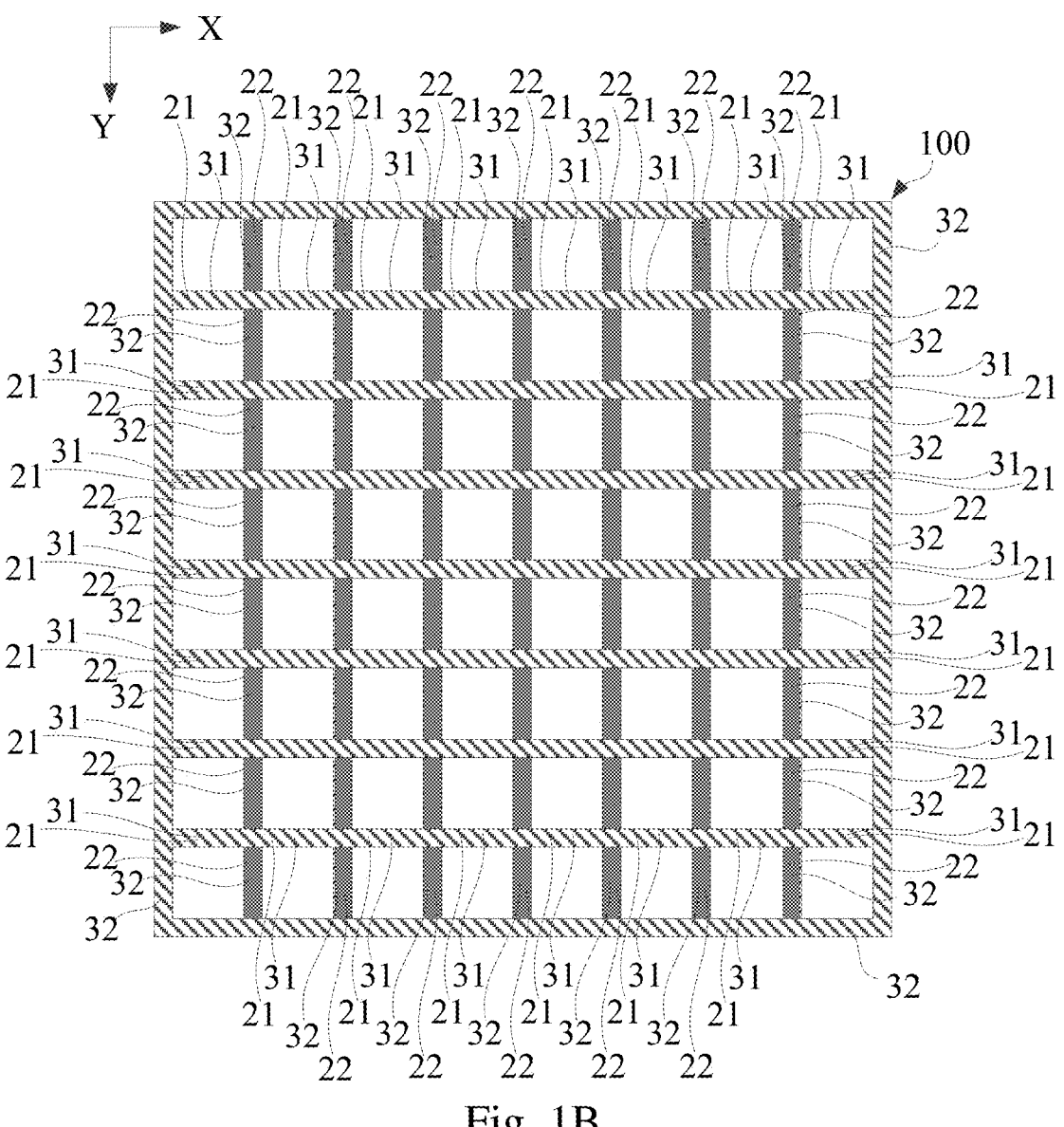
FIG. 1B is a top view of an exemplary scintillation crystal array provided by an embodiment of the application.
Figure 1C:
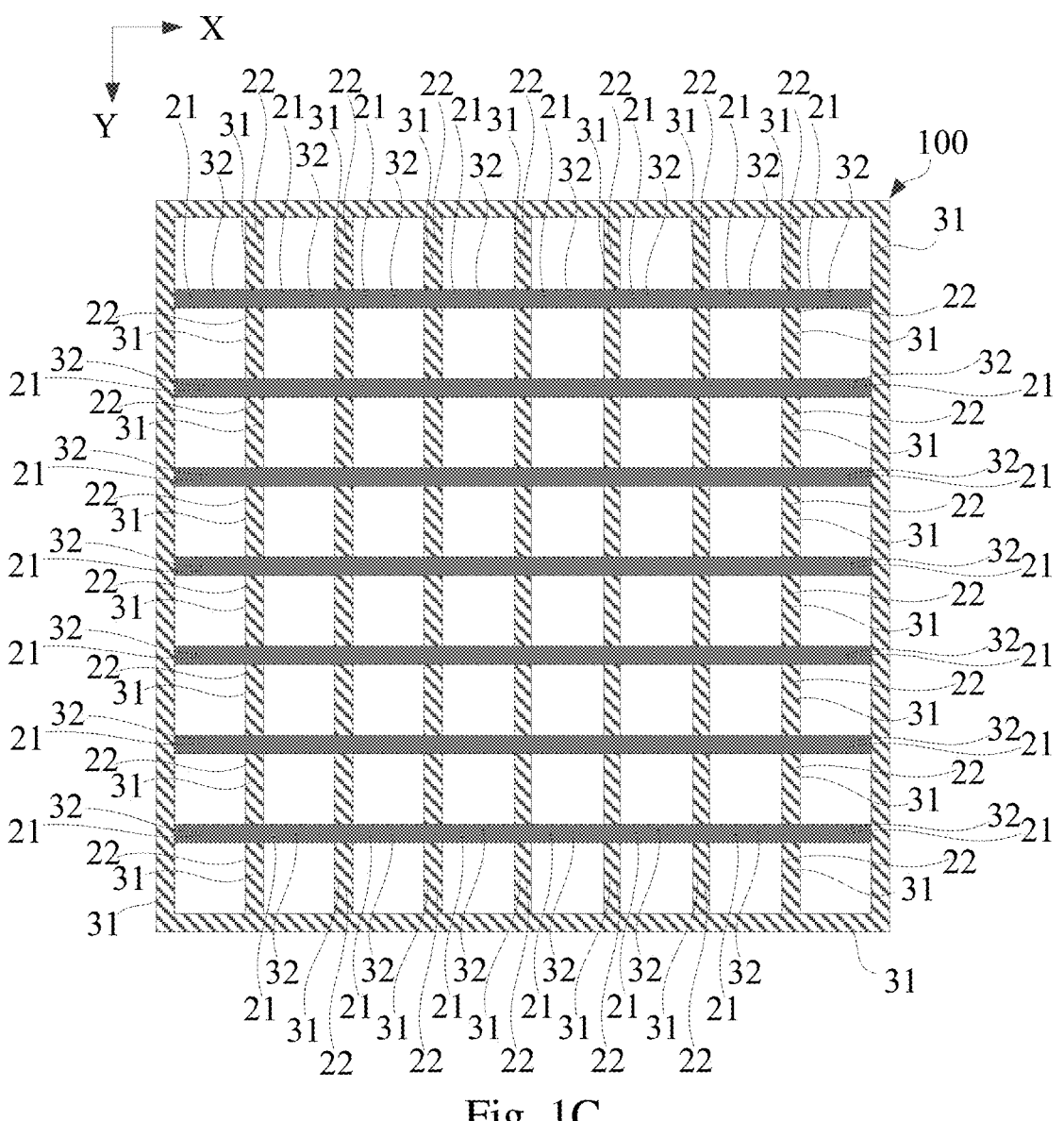
FIG. 1C is a top view of an exemplary scintillation crystal array provided by an embodiment of the application.
Figure 1D:
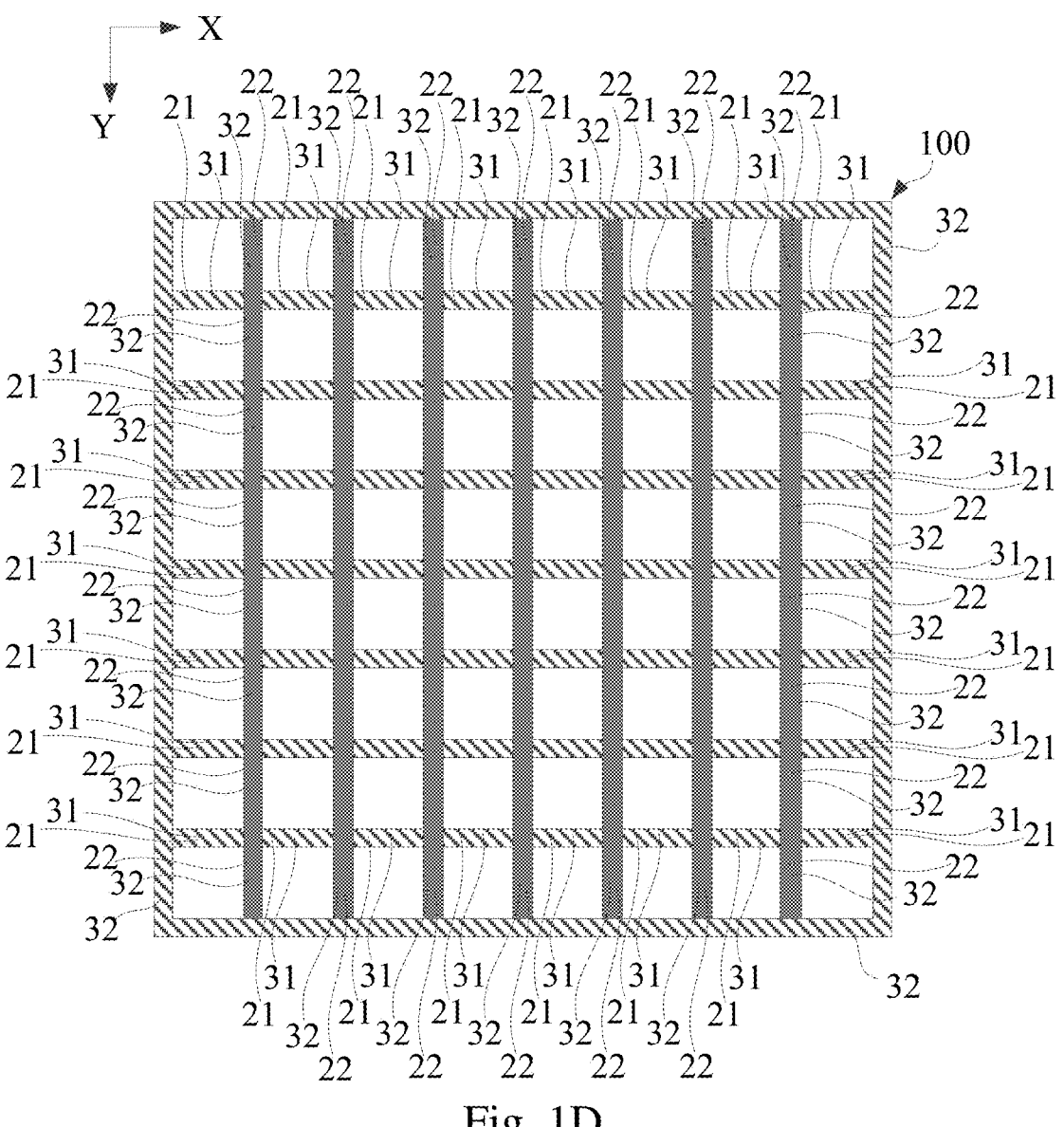
FIG. 1D is a top view of an exemplary scintillation crystal array provided by an embodiment of the application.

In this case, whether it involves filling a part of intersecting gaps 20 with the two kinds of reflecting layers or all intersecting gaps 20 with the two kinds of reflecting layers, ensuring that the gaps in one direction are filled with one type of reflecting layers while the gaps in the other direction are filled with the other type of reflecting layers can reduce the processing difficulty and improve the stability of the whole structure. For example, as shown in FIGS. 1B and 1D, all the first gaps 21 in the X direction in the scintillation crystal array 100 are filled with the first reflecting layers 31, and all the second gaps 22 in the Y direction are filled with the second reflecting layers 32 (of course, as shown in FIGS. 1A and 1C, it is also possible to fill all the first gaps 21 in the X direction with the second reflecting layers 32, and all the second gaps 22 in the Y direction with the first reflecting layers 31). For another example, as shown in FIG. 7, all the first gaps 21 in the X direction in the upper left part A and the lower right part D are filled with the first reflecting layers 31, all the second gaps 22 in the Y direction are filled with the second reflecting layers 32, all the first gaps 21 in the X direction in the upper right part B and the lower left part C are filled with the second reflecting layers 32, and all the second gaps 22 in the Y direction are filled with the first reflecting layers 31. By filling the gaps 20 in a same direction with a same kind of reflecting layers, the manufacturing process can be facilitated by producing entire rows or columns, thereby improving production convenience, efficiency, and overall structural stability.

In some embodiments, when two or more first reflecting layers 31 are adjacently arranged in a same row or column of gaps 20, the two or more first reflecting layers 31 adjacently arranged in a same row or column of gaps 20 are uninterrupted, or gaps between the two or more first reflecting layers 31 adjacently arranged in a same row or column of gaps 20 are filled with intersecting second reflecting layers 32.

In this case, in order to avoid light leakage or crosstalk between two or more adjacent gaps 20 filled with the first reflecting layers 31 on a same row or column, it is important to maintain there is no gap between the first reflecting layers 31 within the two or more gaps 20. Of course, if there are gaps between two or more adjacent first reflecting layers 31 on a same row or column, they can be filled by the second reflecting layers 32 arranged in a different direction, so as to prevent light leakage or crosstalk.

Several specific application examples shown in FIGS. 1A-1D, FIG. 7 and FIG. 8 are described in detail below.

Application Example 1

As shown in FIG. 1A (or 1C) and FIG. 3, the scintillation crystal array 100 comprises an 8×8 grid of scintillation crystal units 10, which can be made of an LYSO crystal material. The top surfaces 11 of all the scintillation crystal units 10 face one side as the light-emitting surface 101 of the scintillation crystal array 100, coupling with the photoelectric sensor. The bottom surfaces 12 of all the scintillation crystal units 10 face one side as the incident surface 102 of the scintillation crystal array 100. A gap 20 is provided between the inner side surfaces of each two adjacent scintillation crystal units 10, and the thickness of the gap 20 can be between 0.01 mm and 0.5 mm. In the scintillation crystal array 100, all the second gaps 22 in the Y direction are filled with the first reflecting layers 31 (such as ESR reflecting layer, PTFE film, and aluminum foil), and all the first gaps 21 in the X direction are filled with the second reflecting layers 32 (such as barium sulfate reflecting layer, titanium dioxide reflecting layer, and magnesium oxide reflecting layer). The outer side surface 103 and the incident surface 102 of the scintillation crystal array 100 may be provided with thin film reflecting layers such as ESR reflecting layers. By adopting the combination of the two kinds of reflecting layers, there is no light leakage or crosstalk in the whole scintillation crystal array 100, resulting in high light collection efficiency and ensuring the uniformity of the distribution of the scintillation crystal units 10.

Application Example 2

As shown in FIG. 1B (or 1D), the overall structure is similar to that of Application example 1, but the differences are as follows. In the scintillation crystal array 100, all the first gaps 21 in the X direction are filled with the first reflecting layers 31 (such as ESR reflecting layer, PTFE film, and aluminum foil), and all the second gaps 22 in the Y direction are filled with the second reflecting layers 32 (such as barium sulfate reflecting layer, titanium dioxide reflecting layer, and magnesium oxide reflecting layer). The outer side surface 103 and the incident surface 102 of the scintillation crystal array 100 may be provided with thin film reflecting layers such as ESR reflecting layers. By adopting the combination of the two kinds of reflecting layers, there is no light leakage or crosstalk in the whole scintillation crystal array 100, resulting in high light collection efficiency and ensuring the uniformity of the distribution of the scintillation crystal units 10.

Application Example 3

As shown in FIG. 7, the scintillation crystal array 100 comprises an 8×8 grid of scintillation crystal units 10, which can be made of an LYSO crystal material. The scintillation crystal array 100 is divided into four parts. In the upper left part A and the lower right part D, except the gaps 20 adjacent to other parts, all the first gaps 21 in the X direction are filled with the second reflecting layers 32, and all the second gaps 22 in the Y direction are filled with the first reflecting layers 31. In the upper right part B and the lower left part C, except the gaps 20 adjacent to other parts, all the first gaps 21 in the X direction are filled with the first reflecting layers 31, and all the second gaps 22 in the Y direction are filled with the second reflecting layers 32. Adjacent gaps 20 in the four parts are filled with the second reflecting layers 32. In the scintillation crystal array 100 shown in FIG. 7, there is no light leakage or crosstalk, resulting in high light collection efficiency and ensuring the uniformity of the distribution of the scintillation crystal units 10.

Application Example

As shown in FIG. 8, the scintillation crystal array 100 comprises an 8×8 grid of scintillation crystal units 10, which can be made of an LYSO crystal material. In the scintillation crystal array 100 shown in FIG. 8, the two kinds of reflecting layers are arranged in the array in an irregular manner, which also achieves the effect that there is no light leakage or crosstalk in the gaps outside each scintillation crystal unit 10, resulting in high light collection efficiency and ensuring the uniformity of the distribution of the scintillation crystal units 10.

Of course, the above application examples are only for illustration, and are not used to limit this application. In actual application, the arrangement mode of the scintillation crystal units 10 and the arrangement mode of the mixed reflecting layers in the scintillation crystal array 100 can be adjusted as needed.

According to the scintillation crystal array provided by the embodiment of the application, by filling the gaps 20 between the scintillation crystal units 10 with the combination of the first reflecting layers 31 and the second reflecting layer 32, it is possible to leverage the high reflectivity of the thin film-like material while effectively preventing light leakage or crosstalk issues in the scintillation crystal array, thereby improving the light collection efficiency of a detector including the scintillation crystal array, preventing PET image distortion in detector applications, and improving detector performance and PET imaging quality. Moreover, during the flattening of the second reflecting layers 32, the first reflecting layers 31 remain stable and free from misalignment and deformation, thereby ensuring uniform thickness of the reflecting layers and uniform distribution of the scintillation crystal units 10. This enables clear differentiation after decoding of PET images obtained. Especially for ultra-small scintillation crystal arrays, by the combination of the first reflecting layers 31 and the second reflecting layers 32, ultra-high precision light collection efficiency can be achieved to support ultra-precise PET imaging.

An embodiment of the application further provides a method for manufacturing the scintillation crystal array as described in the above embodiment, which comprises the following steps:

arranging the first reflecting layers 31 in a part of the gaps 20 of the scintillation crystal array, and arranging the second reflecting layers 32 in a part of the gaps 20, wherein the first reflecting layers 31 are made of a thin film-like material, and the second reflecting layers 32 are made of an amorphous material.

According to the manufacturing method provided by the embodiment of the application, by filling the gaps 20 between the scintillation crystal units 10 with the combination of the first reflecting layers 31 and the second reflecting layer 32, it is possible to leverage the high reflectivity of the thin film-like material while effectively preventing light leakage or crosstalk issues in the scintillation crystal array, thereby improving the light collection efficiency of a detector including the scintillation crystal array, preventing PET image distortion in detector applications, and improving detector performance and PET imaging quality. Moreover, during the flattening of the second reflecting layers 32, the first reflecting layers 31 remain stable and free from misalignment and deformation, thereby ensuring uniform thickness of the reflecting layers and uniform distribution of the scintillation crystal units 10. This enables clear differentiation after decoding of PET images obtained. Especially for ultra-small scintillation crystal arrays, by the combination of the first reflecting layers 31 and the second reflecting layers 32, ultra-high precision light collection efficiency can be achieved to support ultra-precise PET imaging.

Further, in the above process of manufacturing the scintillation crystal array, the step of arranging the first reflecting layers 31 in a part of the gaps 20 of the scintillation crystal array 100, and arranging the second reflecting layers 32 in a part of the gaps 20 comprises:

splitting the scintillation crystal array 100 into one or more array units while maintaining two or more adjacent first reflecting layers 31 in a same row or column uninterrupted, each array unit comprising one or more rows of scintillation crystal units 10;

arranging each row of scintillation crystal units 10 of each array unit in a column in a second direction (Y direction), top surfaces 11 of the scintillation crystal units 10 facing a same side and bottom surfaces 12 facing a same side, and adjacent scintillation crystal units 10 being spaced apart according to a predetermined gap size, so as to obtain a plurality of first single-row crystals;

taking a plurality of first reflecting layers with a thickness equal to the predetermined gap size, a length equal to a size of the first single-row crystal in the second direction, and a width equal to a size of the first single-row crystal in a third direction (Z direction), and bonding each first reflecting layer to a side surface of one first single-row crystal, an edge of the first reflecting layer being flush with an edge of the first single-row crystal, so as to obtain a plurality of second single-row crystals;

bonding the plurality of second single-row crystals, a side opposite to the side where the first reflecting layer is located in each second single-row crystal being bonded to the side where the first reflecting layer is located in another second single-row crystal, edges of two adjacent second single-row crystals being flush with each other, and each adjacent scintillation crystal units 10 between two adjacent second single-row crystals share a same axis in the first direction (X direction), so as to obtain an array unit;

after a plurality of array units being manufactured, arranging the plurality of array units into an array, adjacent array units being separated by the predetermined gap size, so as to obtain a first crystal array;

filling gaps 20 without the first reflecting layers 31 with the second reflecting layers in the first crystal array in a manner that the second reflecting layers slightly flow over an array surface, flattening the second reflecting layers, and scraping off redundant second reflecting layer materials on the array surface, so as to obtain a second crystal array; and bonding the first reflecting layer to an outer side surface and an incident surface of the second crystal array, an edge of the first reflecting layer being flush with an edge of each surface, so as to obtain the final crystal array after the second reflecting layers are solidified.

According to another implementation of the application, in the above process of manufacturing the scintillation crystal array, the step of arranging the first reflecting layers 31 in a part of the gaps 20 of the scintillation crystal array 100, and arranging the second reflecting layers 32 in a part of the gaps 20 comprises:

manufacturing a plurality of single-row crystals;

bonding two sides of each of a plurality of first reflecting layers 31 with a thickness equal to a predetermined gap size, a length equal to a size of the single-row crystals in a second direction (Y direction), and a width equal to a size of the single-row crystals in a third direction (Z direction) to side surfaces of two adjacent single-row crystals respectively, an edge of the first reflecting layer 31 being flush with an edge of the single-row crystal, so as to obtain a first crystal array;

cutting the first crystal array into a plurality of single-row crystals in a first direction (X direction), so that each single-row crystal comprises a plurality of scintillation crystal units 10 and a plurality of first reflecting layers 31 sandwiched therebetween;

setting the gap 20 between each two adjacent single-row crystals to be the same as the predetermined gap size;

filling the gaps 20 between each two adjacent single-row crystals with the second reflecting layers 32 in a manner that the second reflecting layers 32 slightly flow over an array surface, flattening the second reflecting layers, and scraping off redundant second reflecting layer materials on the array surface, so as to obtain a second crystal array; wherein it should be noted that the steps for filling the second reflecting layers 32 can be done in a sequential manner, one row at a time; alternatively, it is also possible to combine each two adjacent single-row crystals to form multiple double-row crystals, and then fill the second reflecting layers 32 in the gaps between each double-row crystal, and so on; and any other appropriate sequence of operations can also be employed; and bonding the first reflecting layers to an outer side surface and an incident surface of the second crystal array, an edge of the first reflecting layer being flush with an edge of each surface, so as to obtain the final scintillation crystal array after the second reflecting layers are solidified.

The manufacturing method will be further described in detail with specific application examples.

For convenience of explanation, the following embodiments assume the use of LYSO for the scintillation crystal unit 10, ESR for the first reflecting layer 31, and barium sulfate for the second reflecting layer 32. However, it should be understood that this is only an example, and the materials of the scintillation crystal unit 10, the first reflecting layer 31, and the second reflecting layer 32 in the embodiment of the application are not limited to these choices, and other materials with the same properties (such as the other materials listed above) can achieve the same results.

The structure of the scintillation crystal array 100 shown in FIGS. 1A and 3 can be seen by referring to the above scintillation crystal array embodiment, which will not be repeated here, and its exemplary manufacturing process may comprise the following steps.

Individual crystal manufacturing: produce 64 LYSO scintillation crystal units 10, each having the same size (specific dimensions can be determined according to actual requirements) and shape as a rectangular prism, with smooth top surface 11 and side surfaces 13 and rough bottom surface 12.

It should be noted that the specific manufacturing process of individual scintillation crystal units 10 is not limited in the embodiment of this application, and any known method in the prior art can be adopted.

Single-row crystal manufacturing: as shown in FIG. 5, arrange eight scintillation crystal units 10 in a column in the Y direction, with the smooth top surfaces 11 of all the scintillation crystal units 10 facing a same side and rough bottom surfaces 12 facing a same side, and a spacing of 0.3 mm (or as adjusted according to actual requirements) between adjacent scintillation crystal units 10, resulting in a first single-row crystal; and repeat the above steps until obtaining eight first single-row crystals.

Internal ESR reflecting layer manufacturing: take an ESR thin film with a thickness similar to the size of the gap 20 between the scintillation crystal units 10 (for example, 0.25 mm-0.3 mm), a length the same as the size of the first single-row crystal in the Y direction, and a width the same as the size of the first single-row crystal in the Z direction, and bond the ESR thin film to a side surface of the first single-row crystal by chemical glue or other materials, with an edge of the ESR thin film being flush with an edge of the first single-row crystal, resulting in a second single-row crystal; and repeat the above steps until obtaining eight second single-row crystals.

Array splicing: as shown in FIG. 5, bond a side opposite to the side where the ESR thin film is located in a second single-row crystal to the side where the ESR thin film is located in another second single-row crystal by chemical glue or other materials, with edges of the two single-row crystals being flush with each other, and each two adjacent scintillation crystal units 10 between the two single-row crystals sharing a same axis in the X direction; and repeat the above steps until the combination of eight single-row crystals is completed, and a first crystal array is obtained.

Internal barium sulfate reflecting layer manufacturing: fill each gap in the X direction of the first crystal array with liquid resin doped with barium sulfate powder in a preset ratio, so that the liquid resin fills the gaps at the intersection positions with the ESR thin film, and flatten the liquid resin; wherein in order to ensure that all the gaps are filled with the liquid resin, the liquid resin can slightly flow over the array surface, and then the extra resin material on the surface can be scraped off; and obtain a second crystal array after the resin is solidified.

External ESR reflecting layer manufacturing: bond ESR thin films to the outer side surface and incident surface of the second crystal array by chemical glue or other materials, with edges of the ESR thin films being flush with edges of each surface, so as to obtain the final crystal array.

Tools and fixtures can be used to fix crystal units and crystal arrays that need to be fixed in the manufacturing process. Moreover, the number of components described above in this embodiment is only exemplary and does not limit the scope of this application. Those skilled in the art can understand that the number of components can be adjusted according to actual needs.

Figure 6:
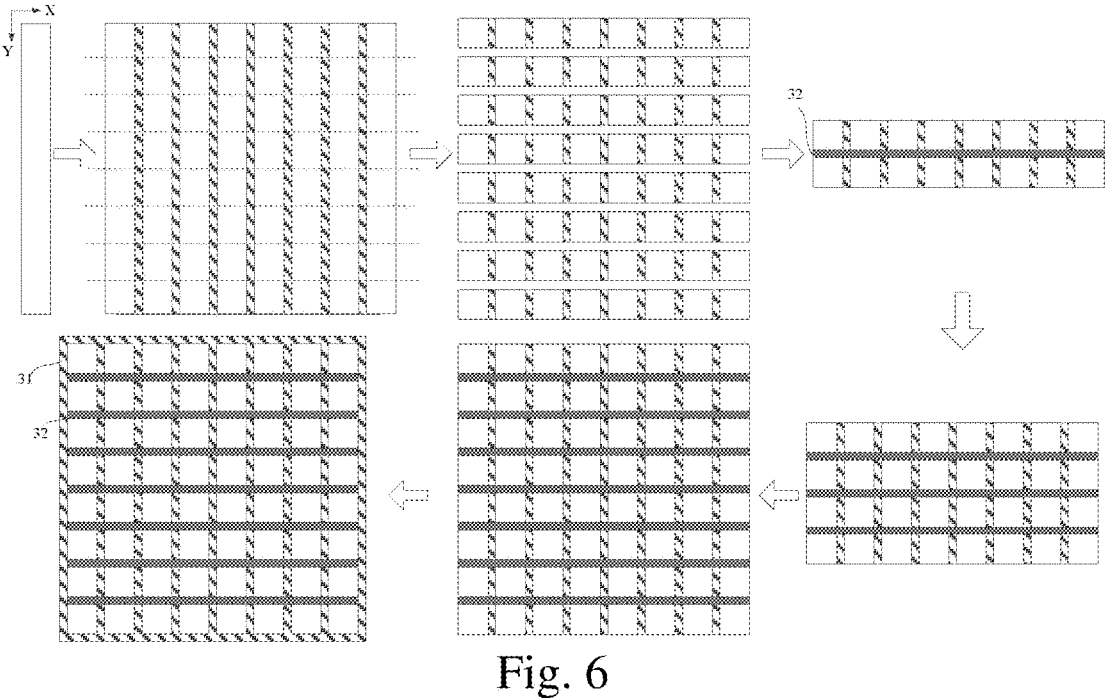
FIG. 6 is a schematic diagram showing the manufacturing of an exemplary scintillation crystal array provided by another embodiment of the application.

FIG. 6 is a schematic diagram showing the manufacturing of a scintillation crystal array 100 provided by another embodiment of the application. As shown in FIG. 6, the exemplary manufacturing process may comprise the following steps (for brevity, the common aspects of this embodiment and the previous embodiment will not be repeated here).

Single-row crystal manufacturing: produce eight LYSO single-row crystals, each having the same size (specific dimensions can be determined according to actual requirements) and shape as a rectangular prism, with smooth top surface 11 and side surfaces 13 and rough bottom surface 12.

It should be noted that the specific manufacturing process of the single-row crystals is not limited in this embodiment, and any known method in the prior art can be adopted.

Array splicing: take seven ESR thin films with a thickness similar to the size of the gap 20 between the scintillation crystal units 10 as shown in FIG. 2 (for example, 0.25 mm-0.3 mm), a length the same as the size of the single-row crystal in the Y direction, and a width the same as the size of the single-row crystal in the Z direction, and bond two sides of each ESR thin film to side surfaces of two adjacent single-row crystals by chemical glue or other materials respectively, with edges of each ESR thin film being flush with edges of the single-row crystals, resulting in a first crystal array.

Array cutting: in the X direction as shown in FIG. 6, cut the first crystal array horizontally into eight single-row crystals, so that each single-row crystal comprises eight scintillation crystal units 10 and seven ESR thin films sandwiched therebetween.

Internal barium sulfate reflecting layer manufacturing: set the gap between each two adjacent single-row crystals to be approximately the same as the gap 20 between the scintillation crystal units 10 as shown in FIG. 2 (for example, 0.25 mm-0.3 mm), fill each gap in the X direction with liquid resin doped with barium sulfate powder in a preset ratio, so that the liquid resin fills the gaps at the intersection positions with the ESR thin film, and flatten the liquid resin; wherein in order to ensure that all the gaps are filled with the liquid resin, the liquid resin can slightly flow over the array surface, and then the extra resin material on the surface can be scraped off; and obtain a second crystal array after the resin is solidified. It should be noted that the steps for filling the barium sulfate reflecting layers can be done in a sequential manner, one row at a time; alternatively, it is also possible to combine each two adjacent single-row crystals to form multiple double-row crystals, and then fill the barium sulfate reflecting layers in the gaps between the double-row crystals, and so on; and any other appropriate sequence of operations can be employed.

External ESR reflecting layer manufacturing: bond ESR thin films to the outer side surface and incident surface of the second crystal array by chemical glue or other materials, with edges of the ESR thin films being flush with edges of each surface, so as to obtain the final crystal array.

Tools and fixtures can be used to fix crystal units and crystal arrays that need to be fixed in the manufacturing process. Moreover, the number of components described above in this embodiment is only exemplary and does not limit the scope of this application. Those skilled in the art can understand that the number of components can be adjusted according to actual needs.

The structure of the scintillation crystal array 100 shown in FIG. 7 can be seen by referring to the above scintillation crystal array embodiment, which will not be repeated here, and its exemplary manufacturing process may comprise the following steps.

Individual crystal manufacturing: produce 64 LYSO scintillation crystal units 10, each having the same size (specific dimensions can be determined according to actual requirements) and shape as a rectangular prism, with smooth top surface 11 and side surfaces 13 and rough bottom surface 12.

It should be noted that the specific manufacturing process of individual scintillation crystal units 10 is not limited in the embodiment of this application, and any known method in the prior art can be adopted.

The scintillation crystal array is divided into four array units (upper left part A, upper right part B, lower left part C, and lower right part D), wherein each array unit comprises a 4×4 grid of scintillation crystal units 10.

Manufacturing of Upper Left Part A:

Single-row crystal manufacturing: arrange four scintillation crystal units 10 in a column in the Y direction, with the smooth top surfaces 11 of all the scintillation crystal units 10 facing a same side and rough bottom surfaces 12 facing a same side, and a spacing of 0.3 mm (or as adjusted according to actual requirements) between adjacent scintillation crystal units 10, resulting in a first single-row crystal; and repeat the above steps until obtaining four first single-row crystals.

Internal ESR reflecting layer manufacturing: take an ESR thin film with a thickness similar to the size of the gap 20 between the scintillation crystal units 10 (for example, 0.25 mm-0.3 mm), a length the same as the size of the first single-row crystal in the Y direction, and a width the same as the size of the first single-row crystal in the Z direction, and bond the ESR thin film to a side surface of the first single-row crystal by chemical glue or other materials, with an edge of the ESR thin film being flush with an edge of the first single-row crystal, resulting in a second single-row crystal; and repeat the above steps until obtaining three second single-row crystals.

Array splicing: bond a side opposite to the side where the ESR thin film is located in a second single-row crystal to the side where the ESR thin film is located in another second single-row crystal by chemical glue or other materials, with edges of the two single-row crystals being flush with each other, and each two adjacent scintillation crystal units 10 between the two single-row crystals sharing a same axis in the X direction; repeat the above steps until the combination of three single-row crystals is completed; and then bond a side of the first single-row crystal without the ESR thin film to the side where the ESR thin film is located in a previous second single-row crystal by chemical glue, so as to obtain a first crystal array group.

Manufacturing of lower right part D: manufacture the lower right part D in the same way as the upper left part A to obtain a second crystal array group.

Manufacturing of Upper Right Part B:

Single-row crystal manufacturing: Arrange four scintillation crystal units 10 in a row in the X direction, with the smooth top surfaces 11 of all the scintillation crystal units 10 facing a same side and rough bottom surfaces 12 facing a same side, and a spacing of 0.3 mm (or as adjusted according to actual requirements) between adjacent scintillation crystal units 10, resulting in a first single-row crystal; and repeat the above steps until obtaining four first single-row crystals.

Internal ESR reflecting layer manufacturing: take an ESR thin film with a thickness similar to the size of the gap 20 between the scintillation crystal units 10 (for example, 0.25 mm-0.3 mm), a length the same as the size of the first single-row crystal in the X direction, and a width the same as the size of the first single-row crystal in the Z direction, and bond the ESR thin film to a side surface of the first single-row crystal by chemical glue or other materials, with an edge of the ESR thin film being flush with an edge of the first single-row crystal, resulting in a second single-row crystal; and repeat the above steps until obtaining three second single-row crystals.

Array splicing: bond a side opposite to the side where the ESR thin film is located in a second single-row crystal to the side where the ESR thin film is located in another second single-row crystal by chemical glue or other materials, with edges of the two single-row crystals being flush with each other, and each two adjacent scintillation crystal units 10 between the two single-row crystals sharing a same axis in the Y direction; repeat the above steps until the combination of three single-row crystals is completed; and then bond a side of the first single-row crystal without the ESR thin film to the side where the ESR thin film is located in a previous second single-row crystal by chemical glue, so as to obtain a third crystal array group.

Manufacturing of lower left part C: manufacture the lower left part C in the same way as the upper right part B to obtain a fourth crystal array group.

Array combination: put the first crystal array group in the upper left part, the second crystal array group in the upper right part, the third crystal array group in the lower left part and the fourth crystal array group in the lower right part, with a gap of 0.3 mm between adjacent crystal array groups (the gap size can also be adjusted according to actual needs), so as to obtain a first crystal array.

Internal barium sulfate reflecting layer manufacturing: fill the gaps without the ESR thin film with liquid resin doped with barium sulfate powder in a preset ratio from the incident surface of the first crystal array, so that the liquid resin fills the gaps at the intersection positions with the ESR thin film, and flatten the liquid resin; wherein in order to ensure that all the gaps are filled with the liquid resin, the liquid resin can slightly flow over the array surface, and then the extra resin material on the surface can be scraped off; and obtain a second crystal array after the resin is solidified.

External ESR reflecting layer manufacturing: bond ESR thin films to the outer side surface and incident surface of the second crystal array by chemical glue or other materials, with edges of the ESR thin films being flush with edges of each surface, so as to obtain the final crystal array.

Tools and fixtures can be used to fix crystal units and crystal arrays that need to be fixed in the manufacturing process.

Similar to the scintillation crystal array as shown in FIG. 7, the scintillation crystal array shown in FIG. 8 can be split into multiple array units, and the principle of splitting is that two or more ESR reflecting layers adjacent to each other in a same row or column are uninterrupted. After each unit is manufactured, they are then assembled to form the entire array unit, then the barium sulfate reflecting layer is manufactured, and finally the scintillation crystal array with mixed reflecting layers is obtained.

The scintillation crystal array manufactured by the manufacturing method provided by the embodiment of the application can realize various processes realized by the scintillation crystal array embodiment, and can achieve the same technical effect, which will not be repeated in the manufacturing method embodiment.

Similarly, the scintillation crystal array provided by the embodiment of the application can realize all the processes realized by the scintillation crystal array manufactured by the manufacturing method embodiment, and can achieve the same technical effect, which will not be repeated in the scintillation crystal array embodiment.

An embodiment of the application also provides a detector, which comprises the scintillation crystal array described in the above embodiment.

The detector provided by the embodiment of the application can realize various processes realized by the scintillation crystal array embodiment, and can achieve the same technical effect, which will not be repeated in the detector embodiment.

An embodiment of the application also provides a medical imaging device, which comprises the detector described in the above embodiment.

The medical imaging device provided by the embodiment of the application can realize various processes realized by the scintillation crystal array embodiment, and can achieve the same technical effect, which will not be repeated in the medical imaging device embodiment.

It should be noted that the terms "comprise", "include" or any other variations thereof are intended to encompass non-exclusively, such that a process, method, article, or apparatus that comprises a series of elements not only comprises those elements but may also comprise other elements not explicitly listed or inherently present in such process, method, article, or apparatus. In the absence of further limitations, elements limited by the phrase "comprising a . . . " are not excluded from having additional identical elements in the process, method, article, or apparatus that comprises the described elements. In addition, it should be pointed out that the scope of the methods and devices in the implementations of the application is not limited to the order indicated or discussed for executing functions. It may also include executing functions in a fundamentally simultaneous manner or in the opposite order according to the functions involved. For example, the described method can be performed in a different order from that described, and various steps can be added, omitted, or combined. In addition, features described with reference to some examples can be combined in other examples.

The embodiments of this application have been described above with the attached drawings, but this application is not limited to the above specific implementations, which are only schematic, not restrictive. Under the inspiration of this application, those of ordinary skill in the art can make various modifications without departing from the purpose of this application and the scope protected by the claims, which are all within the scope of this application.

What is claimed is:

1. A scintillation crystal array, comprising: a plurality of scintillation crystal units, and a gap provided between each two adjacent scintillation crystal units, wherein first reflecting layers are arranged in a part of the gaps of the scintillation crystal array, second reflecting layers are arranged in a part of the gaps, the first reflecting layers are made of a thin film-like material, and the second reflecting layers are made of an amorphous material;

wherein the gaps comprise first gaps arranged in a first direction and second gaps arranged in a second direction; and a part of intersecting first gaps and second gaps in the scintillation crystal array are respectively provided with the first reflecting layers and the second reflecting layers; or all intersecting first gaps and second gaps in the scintillation crystal array are respectively provided with the first reflecting layers and the second reflecting layers.

2. The scintillation crystal array according to claim 1, wherein in a case where a part of intersecting first gaps and second gaps in the scintillation crystal array are respectively provided with the first reflecting layers and the second reflecting layers, the second reflecting layers are arranged in gaps in the scintillation crystal array except the said part of intersecting first gaps and second gaps.

3. The scintillation crystal array according to claim 1, wherein in the first gaps and the second gaps respectively provided with the first reflecting layers and the second reflecting layers, all the first gaps are provided with the first reflecting layers and all the second gaps are provided with the second reflecting layers, or all the first gaps are provided with the second reflecting layers and all the second gaps are provided with the first reflecting layers.

4. The scintillation crystal array according to claim 1, wherein the first reflecting layers comprise one or more of: ESR reflecting layers, polyethylene terephthalate reflecting layers, polytetrafluoroethylene film reflecting layers, aluminum foil reflecting layers and aluminum-plated plastic reflecting layers.

5. The scintillation crystal array according to claim 1, wherein the second reflecting layers comprise one or more of: reflecting layers made of powder materials, reflecting layers made of liquid materials, reflecting layers made of a mixture of powder materials and liquid materials, and reflecting layers made of paste materials.

6. The scintillation crystal array according to claim 5, wherein the second reflecting layers comprise one or more of: barium sulfate reflecting layers, titanium dioxide reflecting layers, magnesium oxide reflecting layers and polytetrafluoroethylene powder reflecting layers.

7. The scintillation crystal array according to claim 1, wherein a thickness of the gap is greater than or equal to 0.01 mm and less than or equal to 0.5 mm.

8. The scintillation crystal array according to claim 1, wherein the first reflecting layers and the second reflecting layers are distributed in a regular or irregular manner.

9. A detector, comprising the scintillation crystal array according to claim 1.

10. A method for manufacturing the scintillation crystal array according to claim 1, comprising:

arranging the first reflecting layers in a part of the gaps of the scintillation crystal array, and arranging the second reflecting layers in a part of the gaps, wherein the first reflecting layer is made of a thin film-like material, and the second reflecting layer is made of an amorphous material.

11. The method according to claim 10, wherein the step of arranging the first reflecting layers in a part of the gaps of the scintillation crystal array, and arranging the second reflecting layers in a part of the gaps comprises:

splitting the scintillation crystal array into one or more array units while maintaining two or more adjacent first reflecting layers in a same row or column uninterrupted, each array unit comprising one or more rows of scintillation crystal units;

arranging each row of scintillation crystal units of each array unit in a column in a second direction, top surfaces of the scintillation crystal units facing a same side and bottom surfaces facing a same side, and adjacent scintillation crystal units being spaced apart according to a predetermined gap size, so as to obtain a plurality of first single-row crystals;

taking a plurality of first reflecting layers with a thickness equal to the predetermined gap size, a length equal to a size of the first single-row crystal in the second direction, and a width equal to a size of the first single-row crystal in a third direction, and bonding each first reflecting layer to a side surface of one first single-row crystal, an edge of the first reflecting layer being flush with an edge of the first single-row crystal, so as to obtain a plurality of second single-row crystals;

bonding the plurality of second single-row crystals, a side opposite to the side where the first reflecting layer is located in each second single-row crystal being bonded to the side where the first reflecting layer is located in another second single-row crystal, edges of two adjacent second single-row crystals being flush with each other, and each adjacent scintillation crystal units between two adjacent second single-row crystals share a same axis in the first direction, so as to obtain the array units;

after a plurality of array units being manufactured, arranging the plurality of array units into an array, adjacent array units being separated by the predetermined gap size, so as to obtain a first crystal array;

filling gaps without the first reflecting layers with the second reflecting layers in the first crystal array in a manner that the second reflecting layers slightly flow over an array surface, flattening the second reflecting layers, and scraping off redundant second reflecting layer materials on the array surface, so as to obtain a second crystal array; and bonding the first reflecting layers to an outer side surface and an incident surface of the second crystal array, an edge of the first reflecting layer being flush with an edge of each surface, so as to obtain the scintillation crystal array after the second reflecting layers are solidified.

12. The method according to claim 10, wherein the step of arranging the first reflecting layers in a part of the gaps of the scintillation crystal array, and arranging the second reflecting layers in a part of the gaps comprises:

manufacturing a plurality of single-row crystals;

bonding two sides of each of a plurality of first reflecting layers with a thickness equal to a predetermined gap size, a length equal to a size of the single-row crystals in a second direction, and a width equal to a size of the single-row crystals in a third direction to side surfaces of two adjacent single-row crystals, an edge of the first reflecting layer being flush with an edge of the single-row crystal, so as to obtain a first crystal array;

cutting the first crystal array into a plurality of single-row crystals in a first direction, so that each single-row crystal comprises a plurality of scintillation crystal units and a plurality of first reflecting layers sandwiched therebetween;

setting the gap between each two adjacent single-row crystals to be the same as the predetermined gap size;

filling the gaps between each two adjacent single-row crystals with the second reflecting layers in a manner that the second reflecting layers slightly flow over an array surface, flattening the second reflecting layers, and scraping off redundant second reflecting layer materials on the array surface, so as to obtain a second crystal array; and bonding the first reflecting layers to an outer side surface and an incident surface of the second crystal array, an edge of the first reflecting layer being flush with an edge of each surface, so as to obtain the scintillation crystal array after the second reflecting layers are solidified.

13. The method according to claim 10, wherein the first reflecting layers and the second reflecting layers are distributed in a regular or irregular manner.

* * * * *